US008455194B2

(12) United States Patent
Link et al.

(10) Patent No.: US 8,455,194 B2
(45) Date of Patent: *Jun. 4, 2013

(54) DIAGNOSTIC METHODS

(75) Inventors: Emma Link, Oxford (GB); Sarah Parish, Oxford (GB); Rory Collins, Oxford (GB); Mark Lathrop, Paris (FR)

(73) Assignee: Isis Innovation Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/408,672

(22) Filed: Feb. 29, 2012

(65) Prior Publication Data

US 2012/0202205 A1 Aug. 9, 2012

Related U.S. Application Data

(63) Continuation of application No. 12/920,297, filed as application No. PCT/GB2009/000547 on Feb. 27, 2009.

(30) Foreign Application Priority Data

Feb. 29, 2008 (GB) .................................. 0803833.3
Jul. 7, 2008 (GB) .................................. 0812414.1

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ........................... 435/6.1; 435/91.1; 536/23.1

(58) Field of Classification Search
None
See application file for complete search history.

(56) References Cited

FOREIGN PATENT DOCUMENTS

| EP | 1 186 672 B1 | 11/2005 |
| WO | WO 2006/008656 A2 | 1/2006 |
| WO | WO 2007/061995 A2 | 5/2007 |

OTHER PUBLICATIONS

Robinson (Expert Opin. Pharmacother. 2007, vol. 8, pp. 2159-2172).*
Morimoto et al; Candidate gene approach for the study of genetic factors involved in HMG-CoA reductase inhibitor-induced rhabdomyolysis, eighteenth JSSX Annual Meeting, 8PE-32 (2003) (in Japanese).*
English translation, pp. 1-4, of Morimoto 2003 abstract from Eighteenth JSSX Annual Meeting , 8PE-32.*
Lucentini (The Scientist; 2004, vol. 24, p. 20).*
Hegele (Arterioscler. Thromb. Vasc. Biol.; 2002, vol. 22, pp. 1058-1061).*
Cholesterol Treatment Trialists' (CTT) Collaborators, "Efficacy and safety of cholesterol-lowering treatment: prospective meta-analysis of data from 90,056 participants in 14 randomised trials of statins," Lancet, 2005, pp. 1267-1278, vol. 366.
Thompson, P.D., et al., "Statin-associated myopathy," JAMA, 2003, pp. 1681-1690, vol. 289.
Armitage, J., "The safety of statins in clinical practice," Lancet, 2007, pp. 1781-1790, vol. 370.
Link, E., et al., "SLCOIBI variants and statin-induced myopathy—a genomewide study," N Engl J Med, 2008, pp. 789-799, vol. 359.
Corsini, A., et al., "Pharmacokinetic interactions between statins and fibrates," Am J. Cardiol, 2005, pp. 44K-49K, vol. 96, discussion, pp. 34K-35K.
Law, M., et al., "Statin safety: a systematic review," Am J. Cardiol, 2006, pp. S52-S60, vol. 97.
Ballantyne, C.M., et al., "Risk for myopathy with statin therapy in high-risk patients," Arch Intern Med, 2003, pp. 553-564, vol. 163.
Molden, E., "Variability in Cytochrome P450-Mediated Metabolism of Cardiovascular Drugs: Clinical Implications and Practical Attempts to Avoid Potential Problems," Heart Drug, 2004, pp. 55-79, vol. 4.
Simonson, S.G., et al., "Rosuvastatin pharmacokinetics in heart transplant recipients administered an antirejection regimen including cyclosporine," Clin Pharmacol Ther, 2004, pp. 167-177, vol. 76.
Mangravite, L.M., et al., "Clinical implications of pharmacogenomics of statin treatment," Pharmacogenomics J, 2006, pp. 360-374, vol. 6.
Konig, J., et al., "Pharmacogenomics of human OATP transporters, Naunyn Schmiedebergs Arch Pharmacol," 2006, pp. 432-443, vol. 372.
Shitara, Y., et al., "Pharmacokinetic and pharmacodynamic alterations of 3-hydroxy- 3-methylglutaryl coenzyme A (HMG-CoA) reductase inhibitors: drug-drug interactions and interindividual differences in transporter and metabolic enzyme functions," Pharmacol Ther, 2006, pp. 71-105, vol. 112.
Kajinami, K., et al., "CYP3A4 genotypes and plasma lipoprotein levels before and after treatment with atorvastatin in primary hypercholesterolemia," Am J Cardiol, 2004, pp. 104-107, vol. 93.
Oh, J., et al., "Genetic determinants of statin intolerance," Lipids Health Dis, 2007, pp. 6:7.
Morimoto, K, et al., "OATP-C(OATP01B1)*15 is associated with statin-induced myopathy in hypercholesterolemic patients," Clinical Pharmacology & Therapeutics, 2005, pp. P21-P21 vol. 77.
Kim, K.T., et al., "Increased systemic exposure to rosuvastatin in Asian subjects residing in the United States compared to Caucasian subjects," Clinical Pharmacology and Therapeutics, 2008, p. S 14, vol. 83, Abstract.
Search Study Collaborative Group, "Study of the effectiveness of additional reductions in cholesterol and homocysteine (SEARCH): characteristics of a randomized trial among 12064 myocardial infarction survivors," Am Heart J, 2007, pp. 815-823, vol. 154, No. e6.
Gunderson, K.L., et al., "Whole-genome genotyping of haplotype tag single nucleotide polymorphisms," Pharmacogenomics, 2006, pp. 641-648, vol. 7.

(Continued)

*Primary Examiner* — Jehanne Sitton
(74) *Attorney, Agent, or Firm* — Neifeld IP Law, P.C.

(57) ABSTRACT

This invention relates to a method of determining the susceptibility of an individual to statin-induced myopathy, comprising detecting the presence or absence of one or more polymorphisms in the SLCO1B1 gene in a biological sample from an individual, whereby the presence of one or more polymorphisms indicates that the individual has altered susceptibility to statin-induced myopathy.

14 Claims, 3 Drawing Sheets

OTHER PUBLICATIONS

International Hapmap Consortium, "A haplotype map of the human genome," Nature, 2005, pp. 1299-1320, vol. 437.

Price, A.L., et al., "Principal components analysis corrects for stratification in genome-wide association studies," Nat Genet, 2006, pp. 904-909, vol. 38.

Devlin, B., et al., "Genomic control for association studies," Biometrics, 1999, pp. 997-1004, vol. 55.

Heart Protection Study Collaborative Group, "MRC/BHF Heart Protection Study of cholesterol lowering with simvastatin in 20,536 high-risk individuals: a randomised placebo-controlled trial," Lancet, 2002, pp. 7-22, vol. 360.

Purcell, S., et al., "PLINK: a tool set for whole-genome association and population-based linkage analyses," Am J Hum Genet, 2007, pp. 559-575, vol. 81.

Wellcome Trust Case Control Consortium, "Genome-wide association study of 14,000 cases of seven common diseases and 3,000 shared controls," Nature, 2007, pp. 661-678, vol. 447.

Barrett, J.C., et al., "Haploview: analysis and visualization of LD and haplotype maps," Bioinformatics, 2005, pp. 263-265, vol. 21.

Sinnwell et al., Statistical Analysis of Haplotypes with Traits and Covariates when Linkage Phase is Ambiguous. R package version 1.3.1. http://mayoresearch.mayo.edu/mayo/research/schaid_lab/software.cfm . 2007, 2007.

R Development Core Team, "R: A Language and Environment for Statistical Computing," Vienna, Austria: R Foundation for Statistical Computing, 2007.

Pasanen, M.K., et al., "Frequencies of single nucleotide polymorphisms and haplotypes of organic anion transporting polypeptide 1B1 SLCO1B1 gene in a Finnish population," Eur J Clin Pharmacol, 2006, pp. 409-415, vol. 62.

Tirona, R.G., et al., "Polymorphisms in OATP-C: identification of multiple allelic variants associated with altered transport activity among European- and African-Americans," J Biol Chem, 2001, pp. 35669-35675, vol. 276.

Zocor datasheet, 2007. http://www.emc.medicines.org.uk/emc/assets/c/htmllDisplayDoc.asp?DocumentID=1201.

Vladutiu, G.D., et al., "Genetic risk factors associated with lipid-lowering drug-induced myopathies, Muscle Nerve," 2006, pp. 153-162, vol. 34.

Niemi et al., "Acute effects of pravastatin on cholesterol synthesis are associated with SLCO1B1 (encoding OATP1B1) haplotype *17," Pharmacogenet. Genomics, vol. 15, No. 5, pp. 303-309, May 15, 2005 (Abstract).

Pasanen et al., "Global analysis of genetic variation in SLCO1B1," Pharmacogenomics, vol. 9, No. 1, pp. 19-33, Jan. 2008 (Abstract).

Pasanen et al., "SLCO1B1 polymorphism markedly affects the pharmacokinetics of simvastatin acid," Pharmacogenet. Genomics, vol. 16, No. 12, pp. 873-879, Dec. 2006 (Abstract).

Nozawa et al., "Genetic Polymorphisms of Human Organic Anion Transporters OATP-C (SLC21A6) and OATP-B (SLC21A9): Allele Frequiences in the Japanese Population and Functional Analysis," The Journal of Phamacology and Experimental Therapeutics, vol. 302, No. 2, pp. 2002.

Xu et al., "Organic anion transporting polypeptide-1B1 haplotypes in Chinese patients," Acta Pharmacologica Sinica, vol. 28, No. 10, pp. 1693-1697, Oct. 28, 2007.

Kim, "3-Hydroxy-3-methylglutaryl-coenzyme A reductase inhibitors (statins) and genetic variability (single nucleotide polymorphisms) in a hepatic drug uptake transporter: What's it all about?," Clinical Pharmacology & Therapeutics, vol. 75, No. 5, pp. 381-385, 2004.

Kameyama et al., "Functional characterization of SLCO1B1 (OATP-C) variants, SLCO1B1*5, SLCO1B1*15 and SCLO1B1*15+C1007G, by using transient expression systems of HeLa and HEK293 cells," Pharmacogenetics and Genomics, vol. 15, No. 7, pp. 513-522.

Morimoto et al., "A Novel Variant Allele of OATP-C (SLCO1B1) Found in a Japanese Patient with Pravastatin-induced Myopathy," Drug Metab. Pharmacokinet., vol. 19, No. 6, pp. SNP33(453)-SNP35(455), 2004.

Kivisto et al., "Influence of Drug Transporter Polymorphisms on Pravastatin Pharmacokinetics in Humans," Pharmceutical Research, vol. 24, No. 2, pp. 239-247, Feb. 2007.

Shitara et al., "Pharmacokinetic and pharmacodynamic alterations of 3-hydroxy-3-methylglutaryl coenzyme A (HMG-CoA) reductase inhibitors: Drug-drug interactions and interindividual differences in transporter and metabolic enzyme functions," Pharmacology & Therapeutics, vol. 112, pp. 71-105, 2006.

International Search Report issued in application No. PCT/GB2009/000547 on May 11, 2009.

United Kingdom Search Report issued in application No. GB0803822.3 on Jun. 27, 2008.

Streiner et al., "Correction for Multiple Testing, Is there a resolution?," Chest, vol. 140, No. 1, pp. 16-18, Jul. 2011.

Mikko Niemi et al., Organic Anion Transporting Polypeptide 1B1: a Genetically Polymorphic Transporter of Major Importance for Hepatic Drug Uptake, Pharmacological Reviews, vol. 63, No. 1, 2011, pp. 157-181.

The SEARCH Collaborative Group, The New England Journal of Medicine, SLCO1B1 Variants and Statin-Induced Myopathy—A Genomewide Study, vol. 359, No. 8, Aug. 21, 2008, pp. 789-799.

Deepak Voora et al., The SLCO1B18*5 Genetic Variant is Associated with Statin-Induced Side Effects, Journal of the American College of Cardiology, vol. 54, No. 17, 2009, pp. 1609-1616.

Hironobu Akao et al., Genetic Variation at the SLCO1B1 Gene Locus and Low Density Lipoprotein Cholesterol Lowering Response to Pravastatin in the Elderly, Atherosclerosis, 220, 2012, pp. 413-417.

Hermann et al., "Pharmacokinetics and Drug Disposition: Exposure of atorvastatin is unchanged but lactone and acid metabolites are increased several-fold in patients with atorvastatin-induced myopathy," Clinical Pharmacology & Therapeutics, vol. 79, No. 6, pp. 532-539, 2006.

The SEARCH Collaborative Group, The New England Journal of Medicine, SLCO1B1 Variants and Statin-Induced Myopathy—A Genomewide Study, vol. 359, No. 8, Aug. 21, 2008, pp. 789-799 and Supplementary Appendix, pp. 1-30.

Frudakis et al., "CYP2D6*4 polymorphism is associated with statin-induced muscle effects," Pharmacogenetics and Genomics, vol. 17, pp. 695-707, 2007.

Fiegenbaum et al., "The role of common variants of *ABCB1*, *CYP3A4*, and *CYP3A5* genes in lipid-lowering efficacy and safety of simvastatin treatment," Clin. Pharmocol. Ther., vol. 78, pp. 551-558, 2005.

Zuccaro et al., "Tolerability of statins is not linked to CYP450 polymorphisms, but reduced CYP2D6 metabolism improves cholesteraemic response to simvastatin and fluvastatin," Pharmacological Research, vol. 55, pp. 310-317, 2007.

Mulder et al., "Association of polymorphism in the cytochrome CYP2D6 and the efficacy and tolerability of simvastatin," Clin. Pharmacol. Ther., vol. 70, pp. 546-551, 2001.

Ruano et al., "Physiogenomic Association of Statin-Related Myalgia to Serotonin Receptors," Muscle Nerve, vol. 36, pp. 329-335, 2007.

Bland et al., "Multiple significance tests: the Bonferroni method," BMJ, vol. 310, p. 170, Jan. 21, 1995.

\* cited by examiner

SEQUENCE LISTING

<160> NUMBER OF SEQ ID NOS: 51

<210> SEQ ID NO 1
<211> LENGTH: 22
<212> TYPE: DNA
<213> ORGANISM: Artificial
<220> FEATURE:
<223> OTHER INFORMATION: PCR primer

<400> SEQUENCE: 1
aatggtcttg cagttaattg gg                                        22

```
<210> SEQ ID NO 2
<211> LENGTH: 22
<212> TYPE: DNA
<213> ORGANISM: Artificial
<220> FEATURE:
<223> OTHER INFORMATION: PCR primer

<400> SEQUENCE: 2
tcccttcacc ctgtatcaaa ct                                              22

<210> SEQ ID NO 3
<211> LENGTH: 21
<212> TYPE: DNA
<213> ORGANISM: Artificial
<220> FEATURE:
<223> OTHER INFORMATION: sequencing primer

<400> SEQUENCE: 3
tggcaactgg agtgaactct t                                               21

<210> SEQ ID NO 4
<211> LENGTH: 20
<212> TYPE: DNA
<213> ORGANISM: Artificial
<220> FEATURE:
<223> OTHER INFORMATION: sequencing primer

<400> SEQUENCE: 4
ttccctctac tcccaccctt                                                 20

<210> SEQ ID NO 5
<211> LENGTH: 20
<212> TYPE: DNA
<213> ORGANISM: Artificial
<220> FEATURE:
<223> OTHER INFORMATION: PCR primer

<400> SEQUENCE: 5
tctactctgt gcaaggggct                                                 20

<210> SEQ ID NO 6
<211> LENGTH: 20
<212> TYPE: DNA
<213> ORGANISM: Artificial
<220> FEATURE:
<223> OTHER INFORMATION: sequencing primer

<400> SEQUENCE: 6
tccagcattg acctagcaga                                                 20

<210> SEQ ID NO 7
<211> LENGTH: 20
<212> TYPE: DNA
<213> ORGANISM: Artificial
<220> FEATURE:
<223> OTHER INFORMATION: PCR primer and sequencing primer

<400> SEQUENCE: 7
tcgtgatcaa tccaaaacca                                                 20

<210> SEQ ID NO 8
<211> LENGTH: 20
<212> TYPE: DNA
<213> ORGANISM: Artificial
<220> FEATURE:
<223> OTHER INFORMATION: PCR primer

<400> SEQUENCE: 8
```

```
tgtttttcag ctggcttcct                                          20

<210> SEQ ID NO 9
<211> LENGTH: 23
<212> TYPE: DNA
<213> ORGANISM: Artificial
<220> FEATURE:
<223> OTHER INFORMATION: PCR primer

<400> SEQUENCE: 9
ggtctaacgt aggttgctct gaa                                      23

<210> SEQ ID NO 10
<211> LENGTH: 21
<212> TYPE: DNA
<213> ORGANISM: Artificial
<220> FEATURE:
<223> OTHER INFORMATION: sequencing primer

<400> SEQUENCE: 10
agaatgtact gccactcccc t                                        21

<210> SEQ ID NO 11
<211> LENGTH: 20
<212> TYPE: DNA
<213> ORGANISM: Artificial
<220> FEATURE:
<223> OTHER INFORMATION: sequencing primer

<400> SEQUENCE: 11
tattgccaaa ttgcctgtga                                          20

<210> SEQ ID NO 12
<211> LENGTH: 23
<212> TYPE: DNA
<213> ORGANISM: Artificial
<220> FEATURE:
<223> OTHER INFORMATION: PCR primer

<400> SEQUENCE: 12
atgccatggt ttattctttt tca                                      23

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
taagtttctc ccccatgtgc                                          20

<210> SEQ ID NO 14
<211> LENGTH: 20
<212> TYPE: DNA
<213> ORGANISM: Artificial
<220> FEATURE:
<223> OTHER INFORMATION: sequencing primer

<400> SEQUENCE: 14
tgtctttgag ggaaggcact                                          20

<210> SEQ ID NO 15
<211> LENGTH: 21
<212> TYPE: DNA
<213> ORGANISM: Artificial
```

-continued

```
<220> FEATURE:
<223> OTHER INFORMATION: sequencing primer

<400> SEQUENCE: 15
gcttcagtga aatgatggga a                                              21

<210> SEQ ID NO 16
<211> LENGTH: 20
<212> TYPE: DNA
<213> ORGANISM: Artificial
<220> FEATURE:
<223> OTHER INFORMATION: PCR primer

<400> SEQUENCE: 16
ataacccact tagcctgggg                                                20

<210> SEQ ID NO 17
<211> LENGTH: 20
<212> TYPE: DNA
<213> ORGANISM: Artificial
<220> FEATURE:
<223> OTHER INFORMATION: PCR primer

<400> SEQUENCE: 17
gctgcctgtg tgttctcaaa                                                20

<210> SEQ ID NO 18
<211> LENGTH: 20
<212> TYPE: DNA
<213> ORGANISM: Artificial
<220> FEATURE:
<223> OTHER INFORMATION: sequencing primer

<400> SEQUENCE: 18
ggggaagata atggtgcaaa                                                20

<210> SEQ ID NO 19
<211> LENGTH: 20
<212> TYPE: DNA
<213> ORGANISM: Artificial
<220> FEATURE:
<223> OTHER INFORMATION: sequencing primer

<400> SEQUENCE: 19
cggcaggttt atcatccagt                                                20

<210> SEQ ID NO 20
<211> LENGTH: 20
<212> TYPE: DNA
<213> ORGANISM: Artificial
<220> FEATURE:
<223> OTHER INFORMATION: PCR primer and sequencing primer

<400> SEQUENCE: 20
ttgtcaaagt ttgcaaagtg                                                20

<210> SEQ ID NO 21
<211> LENGTH: 20
<212> TYPE: DNA
<213> ORGANISM: Artificial
<220> FEATURE:
<223> OTHER INFORMATION: PCR primer and sequencing primer

<400> SEQUENCE: 21
gccaagaatg catggttctt                                                20
```

```
<210> SEQ ID NO 22
<211> LENGTH: 24
<212> TYPE: DNA
<213> ORGANISM: Artificial
<220> FEATURE:
<223> OTHER INFORMATION: PCR primer and sequencing primer

<400> SEQUENCE: 22
ttgtatgatc actttccctt tgtc                                          24

<210> SEQ ID NO 23
<211> LENGTH: 20
<212> TYPE: DNA
<213> ORGANISM: Artificial
<220> FEATURE:
<223> OTHER INFORMATION: PCR primer and sequencing primer

<400> SEQUENCE: 23
cacatcaaca tccaagccac                                               20

<210> SEQ ID NO 24
<211> LENGTH: 21
<212> TYPE: DNA
<213> ORGANISM: Artificial
<220> FEATURE:
<223> OTHER INFORMATION: PCR primer

<400> SEQUENCE: 24
ttcattgctg acccttttctt g                                            21

<210> SEQ ID NO 25
<211> LENGTH: 21
<212> TYPE: DNA
<213> ORGANISM: Artificial
<220> FEATURE:
<223> OTHER INFORMATION: PCR primer

<400> SEQUENCE: 25
gcatcaccca ctaggttctt g                                             21

<210> SEQ ID NO 26
<211> LENGTH: 20
<212> TYPE: DNA
<213> ORGANISM: Artificial
<220> FEATURE:
<223> OTHER INFORMATION: sequencing primer

<400> SEQUENCE: 26
agccatcaag tgcacacaag                                               20

<210> SEQ ID NO 27
<211> LENGTH: 20
<212> TYPE: DNA
<213> ORGANISM: Artificial
<220> FEATURE:
<223> OTHER INFORMATION: sequencing primer

<400> SEQUENCE: 27
ttttgttggt ttctccctgc                                               20

<210> SEQ ID NO 28
<211> LENGTH: 23
<212> TYPE: DNA
<213> ORGANISM: Artificial
<220> FEATURE:
<223> OTHER INFORMATION: PCR primer and sequencing primer

<400> SEQUENCE: 28
```
aaaacagcac ttacgtatga ccc                                   23

<210> SEQ ID NO 29
<211> LENGTH: 20
<212> TYPE: DNA
<213> ORGANISM: Artificial
<220> FEATURE:
<223> OTHER INFORMATION: PCR primer and sequencing primer

<400> SEQUENCE: 29
tgcaacttca aatgcagagc                                        20

<210> SEQ ID NO 30
<211> LENGTH: 20
<212> TYPE: DNA
<213> ORGANISM: Artificial
<220> FEATURE:
<223> OTHER INFORMATION: PCR primer

<400> SEQUENCE: 30
caaacactgc atgttcccac                                        20

<210> SEQ ID NO 31
<211> LENGTH: 22
<212> TYPE: DNA
<213> ORGANISM: Artificial
<220> FEATURE:
<223> OTHER INFORMATION: PCR primer

<400> SEQUENCE: 31
tccatccaag attacagtgg tg                                     22

<210> SEQ ID NO 32
<211> LENGTH: 20
<212> TYPE: DNA
<213> ORGANISM: Artificial
<220> FEATURE:
<223> OTHER INFORMATION: sequencing primer

<400> SEQUENCE: 32
agcaagggga ggaagaacat                                        20

<210> SEQ ID NO 33
<211> LENGTH: 24
<212> TYPE: DNA
<213> ORGANISM: Artificial
<220> FEATURE:
<223> OTHER INFORMATION: sequencing primer

<400> SEQUENCE: 33
tttctctaag ccttactttt ccca                                   24

<210> SEQ ID NO 34
<211> LENGTH: 22
<212> TYPE: DNA
<213> ORGANISM: Artificial
<220> FEATURE:
<223> OTHER INFORMATION: PCR primer

<400> SEQUENCE: 34
cagtgagctg aaaggaatgt ca                                     22

<210> SEQ ID NO 35
<211> LENGTH: 20
<212> TYPE: DNA
<213> ORGANISM: Artificial

```
<220> FEATURE:
<223> OTHER INFORMATION: PCR primer

<400> SEQUENCE: 35
aggaagtgct gacaatgggt                                          20

<210> SEQ ID NO 36
<211> LENGTH: 20
<212> TYPE: DNA
<213> ORGANISM: Artificial
<220> FEATURE:
<223> OTHER INFORMATION: sequencing primer

<400> SEQUENCE: 36
ggcaaagatg gagagcgtaa                                          20

<210> SEQ ID NO 37
<211> LENGTH: 21
<212> TYPE: DNA
<213> ORGANISM: Artificial
<220> FEATURE:
<223> OTHER INFORMATION: sequencing primer

<400> SEQUENCE: 37
agaaaaacct gattgtgccc t                                        21

<210> SEQ ID NO 38
<211> LENGTH: 20
<212> TYPE: DNA
<213> ORGANISM: Artificial
<220> FEATURE:
<223> OTHER INFORMATION: PCR primer

<400> SEQUENCE: 38
ggataattcc tcctcagggc                                          20

<210> SEQ ID NO 39
<211> LENGTH: 22
<212> TYPE: DNA
<213> ORGANISM: Artificial
<220> FEATURE:
<223> OTHER INFORMATION: PCR primer

<400> SEQUENCE: 39
tggaatgtta tcaaatggag ca                                       22

<210> SEQ ID NO 40
<211> LENGTH: 20
<212> TYPE: DNA
<213> ORGANISM: Artificial
<220> FEATURE:
<223> OTHER INFORMATION: sequencing primer

<400> SEQUENCE: 40
tctgcagagg gtaaaaggga                                          20

<210> SEQ ID NO 41
<211> LENGTH: 20
<212> TYPE: DNA
<213> ORGANISM: Artificial
<220> FEATURE:
<223> OTHER INFORMATION: sequencing primer

<400> SEQUENCE: 41
taccctgaga gatgcaaggc                                          20
```

```
<210> SEQ ID NO 42
<211> LENGTH: 20
<212> TYPE: DNA
<213> ORGANISM: Artificial
<220> FEATURE:
<223> OTHER INFORMATION: PCR primer and sequencing primer

<400> SEQUENCE: 42
ggccattcaa ctgtgagctt                                               20

<210> SEQ ID NO 43
<211> LENGTH: 20
<212> TYPE: DNA
<213> ORGANISM: Artificial
<220> FEATURE:
<223> OTHER INFORMATION: PCR primer and sequencing primer

<400> SEQUENCE: 43
taggcccttc actctgccta                                               20

<210> SEQ ID NO 44
<211> LENGTH: 20
<212> TYPE: DNA
<213> ORGANISM: Artificial
<220> FEATURE:
<223> OTHER INFORMATION: PCR primer and sequencing primer

<400> SEQUENCE: 44
ttgggtagat gcagaacaaa                                               20

<210> SEQ ID NO 45
<211> LENGTH: 20
<212> TYPE: DNA
<213> ORGANISM: Artificial
<220> FEATURE:
<223> OTHER INFORMATION: PCR primer

<400> SEQUENCE: 45
tgacatgagg agagttttgg                                               20

<210> SEQ ID NO 46
<211> LENGTH: 20
<212> TYPE: DNA
<213> ORGANISM: Artificial
<220> FEATURE:
<223> OTHER INFORMATION: PCR primer

<400> SEQUENCE: 46
gaaggccaga ggcaactaga                                               20

<210> SEQ ID NO 47
<211> LENGTH: 20
<212> TYPE: DNA
<213> ORGANISM: Artificial
<220> FEATURE:
<223> OTHER INFORMATION: PCR primer

<400> SEQUENCE: 47
gtgggaaagc tgcaaaagaa                                               20

<210> SEQ ID NO 48
<211> LENGTH: 22
<212> TYPE: DNA
<213> ORGANISM: Artificial
<220> FEATURE:
<223> OTHER INFORMATION: sequencing primer

<400> SEQUENCE: 48
```

```
cgttatgccc caataaaaag aa                                                  22

<210> SEQ ID NO 49
<211> LENGTH: 24
<212> TYPE: DNA
<213> ORGANISM: Artificial
<220> FEATURE:
<223> OTHER INFORMATION: sequencing primer

<400> SEQUENCE: 49
agctcctcct ttttaacctc tacc                                                24

<210> SEQ ID NO 50
<211> LENGTH: 20
<212> TYPE: DNA
<213> ORGANISM: Artificial
<220> FEATURE:
<223> OTHER INFORMATION: sequencing primer

<400> SEQUENCE: 50
gctggggcag atagtgaaac                                                     20

<210> SEQ ID NO 51
<211> LENGTH: 20
<212> TYPE: DNA
<213> ORGANISM: Artificial
<220> FEATURE:
<223> OTHER INFORMATION: sequencing primer

<400> SEQUENCE: 51
gcggcaaatg atctaggaaa                                                     20
```

DIAGNOSTIC METHODS

CROSS-REFERENCE TO RELATED APPLICATION

This application is a continuation of U.S. application Ser. No. 12/920,297, filed Feb. 27, 2009, which is a U.S. national stage of PCT/GB09/00547, filed under 35 U.S.C. §371 and published in English, and GB 08 03833.3 filed Feb. 29, 2008 and GB 08 12414.1 filed Jul. 7, 2008. Each of these applications is incorporated herein in its entirety.

TECHNICAL FIELD

The present invention relates to diagnostic methods for detecting the susceptibility of an individual to statin-induced myopathy.

BACKGROUND OF THE INVENTION

The statins are a widely-used class of drugs that lower LDL (low density lipoprotein) cholesterol by inhibiting the enzyme 3-hydroxy-3-methylglutaryl-coenzyme-A (HMG-CoA) reductase and thereby reducing the production of cholesterol by the liver. Large-scale randomised evidence shows that statin therapy reduces the incidence of heart attacks, strokes and revascularisations by about one fifth per 1 mmol/L LDL-cholesterol reduction.[1] The benefits achieved with statin use appear to relate primarily to an individual's absolute risk of such events, and to the absolute size of the LDL cholesterol reduction. The additional benefits seen with more intensive statin therapy have resulted in a trend towards the use of higher doses of statin.

Rarely, statins can cause muscle pain or weakness with elevated blood levels of creatine kinase (i.e. myopathy) and, in a minority of cases, this may lead to muscle breakdown and myoglobin release into the circulation (i.e. rhabdomyolysis) with a risk of renal failure and death.[2] The mechanisms by which statins cause myopathy remain unknown, but they appear to be related to statin concentrations in the blood. The incidence of myopathy is only about one per 10,000 patients per year with standard statin doses (such as 20-40 mg simvastatin daily),[3] but the risk increases (possibly about ten-fold) with higher statin doses (such as 80 mg simvastatin daily[4]). It is also increased by concomitant use of certain drugs that interact to produce raised plasma statin levels. For example, gemfibrozil given concomitantly has been found to increase the area under the statin elimination curve (AUC) by 2-4 fold with several statins and to increase myopathy risk many-fold.[5,6] Concomitant use of cyclosporine and itraconazole, and other drugs that inhibit the CYP3A4 enzyme, has also been shown to increase plasma statin exposure several-fold and has been linked with myopathy.[7,8] These clear associations have led to warnings in the statin drug labels against the concomitant use of particular statin doses and certain other drugs (especially gemfibrozil, cyclosporine and itraconazole).[2]

Such interactions are thought to occur when the statin and the concomitant drug share common metabolic pathways. The gemfibrozil interaction with statins has been postulated to be mediated via the UGT glucuronidation enzyme genes or via several CYP genes.[5,7] Several statins (including lovastatin, simvastatin and atorvastatin) are mainly metabolised via the CYP3A4 enzyme, and it has been concluded that most of the clinically important drug-drug interactions that occur with these statins are attributable to the concurrent use of agents that are potent inhibitors or substrates of CYP3A4.[7]

Pravastatin is not metabolised via the CYP genes, but its plasma level may be influenced by genes involved in its elimination by transportation. Although rosuvastatin metabolism does not appear to depend on the CYP system, several drug interactions of clinical significance are known. For example, when rosuvastatin is combined with cyclosporine, the AUC of rosuvastatin increased 7-11 times and it has been suggested that cyclosporine inhibition of organic anion transport polypeptide C may decrease hepatic uptake of rosuvastatin[9]

The effects of more than 20 genes on statin pharmacokinetics have been investigated.[4,10] For five of these genes (SLCO1B1, CYP3A5, CYP2C9, ABCG2, ABCC2), at least one small study has reported associations with plasma statin levels. The SLCO1B1 gene encodes the organic anion transport protein OATP1B1 that is known to affect the hepatic uptake and biliary excretion of various drugs. In vitro studies indicate that most statins and statin acids are substrates for the SLCO1B1 transporter,[11] although it has been suggested that its contribution to hepatic uptake is lower for lipophilic statins (such as simvastatin and lovastatin) which are thought to be taken up chiefly through passive infusion.[12] A literature search undertaken by the present inventors found that 14 separate reports of the impact of the SLCO1B1 gene on statin pharmacokinetics (mostly involving pravastatin or rosuvastatin) had been published. Not all of the studies yielded statistically significant results, and a combined analysis of them had not previously been performed but the typical impact on statin pharmacokinetics was much smaller than the several-fold increases produced by concomitant use of gemfibrozil or potent CYP3A4 inhibitors.

Consequently, it was not clear whether such differences in statin plasma levels would be of much relevance to the risk of statin-related myopathy.

Some small studies had previously considered the direct relevance to possible statin-related muscle side-effects of various candidate genes, such as CYP3A4 which is involved in the metabolism of certain statins,[13] genes involved in ubiquinone (coenzyme $Q_{10}$) deficiency,[14] and genes encoding organic anion transporting polypeptides (OATP).[11] Associations for myopathy, myalgia or statin intolerance had been reported at "nominal" $p<0.05$ (i.e. before making allowance for the large number of candidate genes and SNPs that were considered) with six genes individually. Given their small size and multiple comparisons however, these small studies did not provide good a priori evidence for any genetic associations with statin-related myopathy. Moreover, apparent differences in myopathy rates in those studies may have been confounded by differences in statin dosages and concomitant use of other drugs.[3] In particular, one study[15] of 10 patients with myopathy and 26 controls reported an association between myopathy among patients taking pravastatin or atorvastatin and the SLCO1B1*15 haplotype (rs4149056 C allele and rs2306283 G allele) with a nominal p-value <0.01. This small study involved the exploration of associations with 152 SNPs in different genes (as well as some haplotype comparisons) and with three separate statins (as well as different combinations of those statins). The impact of this large number of multiple comparisons needs to be allowed for when interpreting the nominal p-values: since not all of the tests would have been independent, the effective number of independent tests was between 300 and 1000. Hence, application of the Bonferroni approach would involve multiplying each nominal p-value by at least 300, rendering a nominal p-value value of 0.01 completely non-significant.

SUMMARY OF THE INVENTION

According to one aspect, the present invention provides a method of determining the susceptibility of an individual to statin-induced myopathy, comprising detecting the presence or absence of one or more polymorphisms in the SLCO1B1 gene in a biological sample from an individual, whereby the presence of one or more polymorphisms indicates that the individual has an altered susceptibility to statin-induced myopathy.

In another aspect, the invention provides a method of reducing the risk of myopathy in an individual during treatment with a statin, comprising
  i) detecting the presence or absence of one or more polymorphisms in the SLCO1B1 gene in a biological sample from an individual;
  ii) classifying the individual according to their susceptibility to statin-induced myopathy, by reference to the presence or absence of the one or more polymorphisms detected in step i); and
  iii) determining a suitable dosage for statin treatment by reference to the susceptibility of the individual to statin-induced myopathy determined in step ii).

Preferably the one or more polymorphisms are selected from the SNP rs4149056 and/or a polymorphism in close linkage with rs4149056, including but not limited to the SNPs rs4363657, rs1871395, rs12317268, rs2900478, rs4149100, rs4149081, rs 11045879, rs7969341, rs11045885, rs12369881, and rs12366582.

In some embodiments, the methods of the invention may also comprise determining the presence or absence of one or more additional polymorphisms in the SLCO1B1 gene, including but not limited to rs2306283, rs 11045819, and rs34671512.

Preferably, the methods of the invention comprise determining whether the genotype of the individual is homozygous or heterozygous for the one or more polymorphisms in the SLCO1B1 gene.

In some embodiments, the methods of the invention involve determining the presence or absence of "high-risk" alleles of one or more polymorphisms that are associated with increased risk of statin-induced myopathy.

In some embodiments, the methods of the invention involve determining the presence or absence of "low-risk" alleles of one or more polymorphisms that are associated with decreased risk of statin-induced myopathy.

Preferably, the methods of the invention involve determining whether the genotype of the individual is homozygous or heterozygous for a cytosine (C) or a thymine (T) at rs4149056.

In other embodiments, the methods of the invention may alternatively, or additionally, involve determining whether the genotype of the individual is homozygous or heterozygous for a guanine (G) or an adenine (A) at rs1871395, rs12317268, rs7969341, rs11045885 or rs12366582; for an A or G at rs4149081 or rs12369881; for a C or T at rs4363657 or rs11045879; for an A or T at rs2900478; or for a deletion of the base from the sequence or A at rs4149100.

In some embodiments, the methods of the invention may also comprise determining whether the genotype of the individual is homozygous or heterozygous for a G or A at rs2306283, for an A or C at rs11045819, or for a C or A at rs34671512.

Preferably, the detection step comprises amplifying at least the part of the nucleic acid sequence encoding the SLCO1B1 gene that contains the one or more polymorphisms, and identifying the nucleotide present in at least one allele of the polymorphism(s) encoded by said amplified DNA.

Preferably, the detection step comprises amplifying exon 6 of the SLCO1B1 gene comprising the SNP rs4149056, more preferably amplifying a nucleic acid sequence containing the nucleotide at position 521 of the SLCO1B1 gene and identifying the nucleotide present at that position.

In other embodiments, the detection step may alternatively, or additionally, comprise amplifying at least the part of intron 8 of the SLCO1B1 gene that comprises the SNPs rs1871395 or rs12317268; at least the part of intron 11 of the SLCO1B1 gene that comprises the SNPs rs4363657, rs2900478 or rs4149100; or at least the part of intron 14 of the SLCO1B1 gene that comprises the SNPs rs4149081, rs11045879, rs7969341, rs11045885, rs12369881, or rs12366582; and identifying the nucleotide present in at least one allele of the one or more polymorphisms encoded by said amplified DNA.

In some embodiments, the methods of the invention may also comprise amplifying at least the part of exon 5 of the SLCO1B1 gene that comprises the SNPs rs2306283, or rs 11045819; or at least the part of exon 15 of the SLCO1B1 gene that comprises the SNP rs34671512; and identifying the nucleotide present in at least one allele of the one or more polymorphisms encoded by said amplified DNA.

Preferably the methods of the invention involve the use of polymerase chain reaction (PCR) using suitable primers adapted to amplify and/or identify the nucleotide present in at least one allele of the one or more polymorphisms.

In some embodiments, said amplification and identification may be conducted in a single step using one or more allele-specific amplification primers.

In other embodiments of methods of the invention, one or more allele-specific probes may be used to identify the nucleotide present in at least one allele of the one or more polymorphisms encoded by the test nucleic acid or said amplified DNA.

In a further aspect, the invention provides a method of determining a suitable dosage for an individual in need of treatment with a statin, comprising
  i) deteimining whether the genotype of the individual is heterozygous or homozygous for one or more polymorphisms in the SLCO1B1 gene in a biological sample from an individual; and
  ii) determining a suitable dosage for statin treatment by reference to the genotype of the individual, whereby a standard dose of a statin is suitable for an individual with a high-risk genotype and a higher dose is suitable for an individual with a low-risk genotype.

In a further aspect, the invention provides a method of treating an individual in need of treatment with a statin, comprising:
  i) determining whether the genotype of the individual is heterozygous or homozygous for one or more polymorphisms in the SLCO1B1 gene in a biological sample from an individual;
  ii) classifying the individual according to their genotype at the one or more polymorphisms as determined in step i); and
  iii) administering a suitable dose of a statin, whereby a standard dose of a statin is suitable for an individual with a heterozygous or homozygous high-risk genotype, and a higher dose is suitable for an individual with a homozygous low-risk genotype.

Preferably, the methods of the invention involve determining a suitable statin and a suitable dosage of that statin for a particular individual (i.e. a statin regimen). Preferably, the methods of the invention comprise determining the genotype of the individual at the SNP rs4149056, wherein a high-risk genotype is defined as a CC or TC genotype, and a low-risk genotype is defined as a TT genotype.

In other embodiments, the methods of the invention may alternatively, or additionally, involve determining the genotype of the individual at the SNPs rs1871395, rs12317268, rs7969341, rs11045885 or rs12366582, wherein a high-risk genotype is defined as a GG or GA genotype, and a low-risk genotype is defined as a AA genotype.

In other embodiments, the methods of the invention may alternatively, or additionally, involve determining the genotype of the individual at the SNPs rs4149081 or rs12369881, wherein a high-risk genotype is defined as a AA or AG genotype, and a low-risk genotype is defined as a GG genotype.

In other embodiments, the methods of the invention may alternatively, or additionally, involve determining the genotype of the individual at the SNPs rs4363657 or rs11045879, wherein a high-risk genotype is defined as a CC or CT genotype, and a low-risk genotype is defined as a TT genotype.

In other embodiments, the methods of the invention may alternatively, or additionally, involve determining the genotype of the individual at the SNP rs2900478, wherein a high-risk genotype is defined as a AA or AT genotype, and a low-risk genotype is defined as a TT genotype.

In other embodiments, the methods of the invention may alternatively, or additionally, involve determining the genotype of the individual at the SNP rs4149100, wherein a high-risk genotype is defined as a genotype that is homozygous for a deletion or heterozygous for a deletion; and a low-risk genotype is defined as a AA genotype.

In a further aspect, the invention provides a method of treating an individual in need of treatment with a statin, comprising
  i) determining whether the genotype of the individual is heterozygous or homozygous for a cytosine (C) or a thymine (T) at the SNP rs4149056 in the SLCO1B1 gene in a biological sample from an individual;
  ii) classifying the individual according to their genotype at rs4149056 determined in step i); and
  iii) administering a suitable dose of a statin, whereby a standard dose of a statin is suitable for an individual with a CC or TC genotype and a higher dose is suitable for an individual with a TT genotype.

The methods of the invention may additionally involve determining a suitable statin regimen (i.e. drug and dosage), or administering a dose of a statin, for or to an individual having an elevated risk of myopathy, wherein the statin is to be used in combination with one or more alternative LDL lowering therapies.

Further aspects provide analogous methods of treating, or determining a suitable regimen (i.e. drug and dosage) for an individual in need of treatment with a statin, comprising the step of detecting the presence or absence of one or more polymorphisms in the SLCO1B1 gene in a biological sample from an individual, wherein the one or more polymorphisms may be a SNP in close linkage with the SNP rs4149056 and/or the SNP rs4363657, including but not limited to rs1871395, rs12317268, rs2900478, rs4149100, rs4149081, rs11045879, rs7969341, rs11045885, rs12369881, or rs12366582.

In one embodiment the statin is selected from the list comprising lovastatin, simvastatin, pravastatin, fluvastatin, atorvastatin, pitavastatin and rosuvastatin.

In preferred embodiments the statin is simvastatin, wherein a standard dose is 20 or 40 mg daily, and a higher dose is 80 mg daily.

In preferred embodiments the methods of the invention can be used for determining a suitable dosage or statin regimen for an individual in need of treatment with a statin, wherein the individual has an increased risk of myopathy, for example through the concomitant use of drugs such as amiodarone, cyclosporine or gemfibrozil that slow statin clearance, or through the decreased hepatic uptake or renal clearance of statins due to genetic variants or disease.

In a further aspect, the invention provides an in-vitro diagnostic kit for screening for susceptibility of an individual to statin-induced myopathy, comprising one or more reagents for detecting the presence or absence of one or more polymorphisms in the SLCO1B1 gene in a biological sample from an individual.

Preferably, the one or more reagents comprise one or more allele-specific amplification primers or allele-specific probes.

Preferably, the one or more reagents comprise allele-specific amplification primers or allele-specific probes capable of determining whether the genotype of the individual is heterozygous or homozygous for the one or more polymorphisms described above.

Preferably, the kits comprise instructions for amplification and/or detection of the alleles of the one or more polymorphisms in the SLCO1B1 gene.

Preferably, the kits comprise instructions which define a suitable dosage for statin treatment by reference to whether the genotype of the individual is heterozygous or homozygous for the one or more polymorphisms, whereby a standard dose of a statin is suitable for an individual with a heterozygous or homozygous high-risk genotype, and a higher dose is suitable for an individual with a homozygous low-risk genotype.

DEFINITIONS

Figure 1:
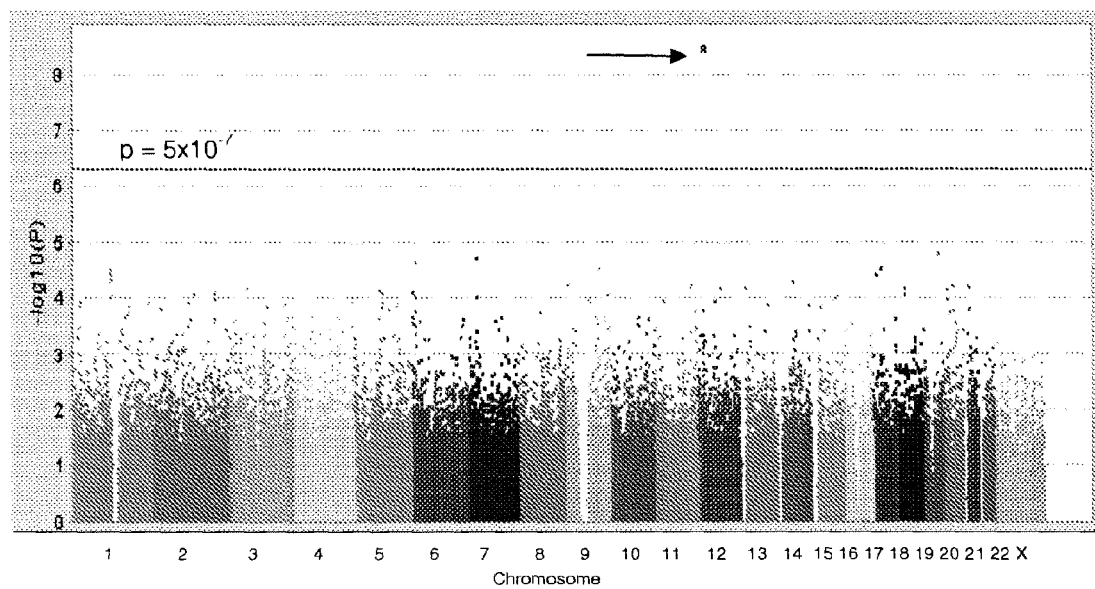
FIG. 1 shows probability values for each SNP measured separately in the initial genome-wide association study of 85 Caucasian myopathy cases and 90 Caucasian controls allocated 80 mg simvastatin daily. Analyses included 316,184 (99.4%) of the 318,237 SNPs on the Sentrix HumanHap300-Duo BeadChip (11-lumina). Results above the horizontal line have individual SNP p-values $<5\times10^{-7}$ (i.e. strong evidence for association). The arrow indicates the SNP rs4363657 with a p-value of $4\times10^{-9}$ (highly significant P=0.001 after correction for the number of SNPs that were measured).

The term "marker" as used herein refers to a segment of DNA with an identifiable physical location on a chromosome. A marker may be a gene or other identifiable nucleic acid sequence, such as an open reading frame, a portion of an intron or an intergenic genomic DNA segment. Preferably the marker is a polymorphic site, preferably a single nucleotide polymorphism.

A "polymorphic site" refers the position in a nucleic acid sequence at which a polymorphism occurs. A polymorphic site may be as small as one base pair.

The term "polymorphism" refers to a genetic variation, or the occurrence of two or more genetically determined alternative sequences at a single genetic locus in a population. Each version of the sequence with respect to the polymorphic site is referred to as an "allele" of the polymorphic site. Preferred polymorphisms have two alleles, with the minor allele occurring at a frequency of greater than 1%, and more preferably greater than 5% or 10% of a selected population. The allelic form occurring most frequently in a selected population is sometimes referenced as the "wildtype" form. The allelic form occurring less frequently in a selected population is sometimes referenced as the "mutant" form. Diploid organisms may be homozygous or heterozygous for allelic forms. A biallelic polymorphism has two forms. A triallelic polymorphism has three forms. Examples of polymorphisms include restriction fragment length polymorphisms (RFLPs), variable number of tandem repeats (VNTRs), single nucleotide polymorphisms (SNPs), dinucleotide repeats, trinucleotide repeats, tetranucleotide repeats, simple sequence repeats, and insertion elements such as Alu.

The term "SNP" or "single nucleotide polymorphism" is a polymorphism that occurs at a polymorphic site occupied by a single nucleotide. The site of the SNP is usually preceded by and followed by highly conserved sequences (e.g., sequences that vary in less than 1/100 or 1/1000 members of a population). As used herein, "SNPs" is the plural of SNP. SNPs are most frequently diallelic. A most common allele of a SNP is called a "major" or "wild-type" allele and an alternative allele of said SNP is called a "minor" or "mutant" allele. A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

SNPs tend to be evolutionarily stable from generation to generation and, as such, can be used to study specific genetic abnormalities throughout a population. If SNPs occur in the protein coding region it can lead to the expression of a variant, sometimes defective, form of the protein that may lead to development of a genetic disease. Such SNPs can therefore serve as effective indicators of the genetic disease. Some SNPs may occur in non-coding regions, but nevertheless, may result in differential or defective splicing, or altered protein expression levels. SNPs can therefore be used as diagnostic tools for identifying individuals with a predisposition for certain diseases, genotyping the individual suffering from the disease in terms of the genetic causes underlying the condition, and facilitating drug development based on the insight revealed regarding the role of target proteins in the pathogenesis process.

A "SNP location" or "SNP locus" is a polymorphic site at which a SNP occurs.

The term "linkage" as used herein refers to the non-random association of alleles at two or more polymorphic sites. The term "close linkage" refers to a measure of linkage disequilibrium having a squared correlation coefficient of $r^2 > 0.8$.

The term "nucleic acid" as used herein, means a single or double-stranded deoxyribonucleotide or ribonucleotide polymer of any length, and include as non-limiting examples, coding and non-coding sequences of a gene, sense and anti-sense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, and fragments thereof. Reference to a polynucleotide(s) is to be similarly understood.

The term "fragment" of a polynucleotide sequence provided herein is a subsequence of contiguous nucleotides that is capable of specific hybridisation to a target of interest, e.g., a sequence that is at least 10 nucleotides in length. The fragments may comprise 10, preferably 15 nucleotides, preferably at least 20 nucleotides, more preferably at least 30 nucleotides, more preferably at least 40 nucleotides, more preferably at least 50 nucleotides and most preferably at least 60 nucleotides of contiguous nucleotides of a polynucleotide. A fragment of a polynucleotide sequence can be used as a primer, a probe, included in a microarray, or used in polynucleotide-based identification methods.

The term "oligonucleotide(s)" are nucleic acids that are usually between 5 and 100 contiguous bases, and often between 5-10, 5-20, 10-20, 10-50, 15-50, 15-100, 20-50, or 20-100 contiguous bases. An oligonucleotide that is longer than about 20 contiguous bases may be referred to as a polynucleotide. A polymorphic site (polymorphism) can occur at any position within an oligonucleotide.

The term "primer" refers to a polynucleotide, usually having a free 3' OH group, that is hybridised to a template and used for priming polymerisation of a polynucleotide complementary to the target.

The term "probe" refers to a polynucleotide that is used to detect a nucleotide sequence that is complementary to the probe, in a hybridisation-based assay. The probe may consist of a "fragment" of a polynucleotide as defined herein.

The term "hybridise under stringent conditions", and grammatical equivalents thereof, refers to the ability of a polynucleotide molecule to hybridise to a target polynucleotide molecule (such as a target polynucleotide molecule immobilised on a DNA or RNA blot, such as a Southern blot or Northern blot) under defined conditions of temperature and salt concentration. The ability to hybridise under stringent hybridisation conditions can be determined by initially hybridising under less stringent conditions then increasing the stringency to the desired stringency.

With respect to polynucleotide molecules greater than about 100 bases in length, typical stringent hybridisation conditions are no more than 25 to 30° C. (for example, 10° C.) below the melting temperature (Tm) of the native duplex (see generally, Sambrook et al, Eds, 1987, Molecular Cloning, A Laboratory Manual, 2nd Ed. Cold Spring Harbor Press; Ausubel et al, 1987, Current Protocols in Molecular Biology, Greene Publishing). Tm for polynucleotide molecules greater than about 100 bases can be calculated by the formula Tm=81.5+0.41% (G+C−log(Na+) (Sambrook et. al, Eds, 1987, Molecular Cloning, A Laboratory Manual, 2nd Ed. Cold Spring Harbor Press; Bolton and McCarthy, 1962, PNAS 84:1390). Typical stringent conditions for a polynucleotide of greater than 100 bases in length would be hybridisation conditions such as prewashing in a solution of 6×SSC, 0.2% SDS; hybridising at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

In one embodiment stringent conditions use 50% formamide, 5×SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulphate at 42° C., with washes at 42° C. in 0.2×SSC and 50% formamide at 55° C., followed by a wash comprising of 0.1×SSC containing EDTA at 55° C.

With respect to polynucleotide molecules having a length less than 100 bases, exemplary stringent hybridisation conditions are 5 to 10° C. below Tm. On average, the Tm of a polynucleotide molecule of length less than 100 bp is reduced by approximately (500/oligonucleotide length)° C.

The term "susceptibility", when used in relation to statin-induced myopathy or any similar phrase such as "propensity" or "pre-disposition", means that certain alleles have been discovered to be associated with, or predictive of, myopathy induced by statin therapy. These "high-risk" alleles may be the minor (or mutant) allele, or the major (or wild-type) allele. These alleles are thus over-represented in frequency or carriage rate in individuals who are at risk of developing statin-induced myopathy compared to individuals who are not susceptible to statin-induced myopathy. Hence, the term "an individual's susceptibility to statin-induced myopathy" refers to a statistically higher, or lower, frequency of statin-induced myopathy in an individual carrying a particular polymorphic allele, or genotype (i.e. allelic or polymorphism pattern) in comparison to the frequency in a member of the population that does not carry the particular polymorphic allele, or genotype.

An individual that carries one or both high-risk alleles at a polymorphic site is said to have a heterozygous or homozygous "high-risk" genotype for that particular polymorphic site, respectively. An individual that does not carry a particular high-risk allele is said to have a homozygous "low-risk" genotype.

The term "myopathy" as used herein refers to any muscle symptom such as pain, weakness or tenderness that is accompanied by an elevated serum creatine kinase concentration and includes myalgia, myositis, myopathy and rhabdomyolysis.

The term "biological sample" as used herein means a biological sample derived from a patient to be screened. The biological sample may be any suitable sample known in the art in which the expression of the selected markers can be detected. Included are individual cells and cell populations obtained from bodily tissues or fluids. Examples of suitable body fluids to be tested are plasma, blood, lymph and urine.

The term "comprising" as used in this specification and claims means "consisting at least in part of", that is to say when interpreting statements in this specification and claims which include the term, the features, prefaced by that term in each statement, all need to be present but other features can also be present. Related terms such as "comprise" and "comprised" are to be interpreted in a similar manner.

DETAILED DESCRIPTION OF THE INVENTION

The present invention is based on the identification that polymorphisms in the SLCO1B1 gene, particularly the single nucleotide polymorphism (SNP) rs4149056 or one or more polymorphisms in close linkage with rs4149056, including but not limited to rs4363657 are strongly associated (unadjusted $p=4\times10^{-9}$) with myopathy. The susceptibility of an individual to statin-induced myopathy that can be attributed to variation in the SLCO1B1 gene is thus the cumulative risk that is produced by the combination of the effects of polymorphisms in the SLCO1B1 gene.

Accordingly, in a first aspect the present invention provides a method of determining the susceptibility of an individual to statin-induced myopathy, comprising detecting the presence or absence of one or more polymorphisms in the SLCO1B1 gene in a biological sample from an individual, whereby the presence of one or more polymorphisms indicates that the individual has an altered susceptibility to statin-induced myopathy.

In another aspect, the invention provides a method of reducing the risk of myopathy in an individual during treatment with a statin, comprising
  i) detecting the presence or absence of one or more polymorphisms in the SLCO1B1 gene in a biological sample from an individual;
  ii) classifying the individual according to their susceptibility to statin-induced myopathy, by reference to the presence or absence of the one or more polymorphisms detected in step i); and
  iii) determining a suitable dosage for statin treatment by reference to the susceptibility of the individual to statin-induced myopathy determined in step ii).

Preferably the one or more polymorphisms are selected from the SNP rs4149056 and/or a polymorphism in close linkage with rs4149056, including but not limited to the SNPs rs4363657, rs1871395, rs12317268, rs2900478, rs4149100, rs4149081, rs11045879, rs7969341, rs11045885, rs12369881, and rs12366582.

In some embodiments, the methods of the invention may also comprise determining the presence or absence of one or more additional polymorphisms in the SLCO1B1 gene, including but not limited to rs2306283, rs11045819, and rs34671512. Other polymorphisms include rs11045818 and rs2291075.

Preferably, the methods of the invention comprise determining whether the genotype of the individual is homozygous or heterozygous for the one or more polymorphisms in the SLCO1B1 gene.

In some embodiments, the methods of the invention involve determining the presence or absence of "high-risk" alleles of one or more polymorphisms that are associated with increased risk of statin-induced myopathy.

In some embodiments, the methods of the invention involve determining the presence or absence of "low-risk" alleles of one or more polymorphisms that are associated with decreased risk of statin-induced myopathy.

An individual that carries one or both high-risk alleles at a polymorphic site can be classified as having a heterozygous or homozygous "high-risk" genotype for that particular polymorphic site, respectively. An individual that does not carry a particular high-risk allele can be classified as having a homozygous "low-risk" genotype.

Preferably, the methods of the invention involve determining whether the genotype of the individual is homozygous or heterozygous for a cytosine (C) or a thymine (T) at rs4149056.

The methods of the invention may alternatively, or additionally, involve determining whether the genotype of the individual is homozygous or heterozygous for a guanine (G) or an adenine (A) at rs1871395, rs12317268, rs7969341, rs11045885 or rs12366582; for an A or G at rs4149081 or rs12369881; for a C or T at rs4363657 or rs11045879; for an A or T at rs2900478; or for a deletion or A at rs4149100.

In some embodiments, the methods of the invention may also comprise determining whether the genotype of the individual is homozygous or heterozygous for a G or A at rs2306283, for an A or C at rs11045819, or for a C or A at rs34671512.

All allele codings are shown as the mutant (minor) or wild-type (major) allele respectively, for the forward orientation (positive strand).

Techniques for determining the presence or absence of particular alleles in the biological sample are known in the art and include, but are not limited to, mutation discrimination techniques based on sequence such as amplification, nucleic acid sequencing, or nucleic acid hybridisation. Many current methods for the detection of allelic variation are reviewed by Nollau et al, Clin. Chem. 43:1114-1120, 1997; and in standard textbooks, for example "Laboratory Protocols for Mutation Detection", Ed. by U. Landegren, Oxford University Press, 1996 and "PCR", $2^{nd}$ Edition by Newton & Graham, BIOS Scientific Publishers Limited, 1997.

In preferred embodiments the present invention comprises a step of isolating a nucleic acid comprising the one or more polymorphisms to be detected.

The nucleic acid tested can be isolated from the biological sample using a variety of techniques known in the art. By way of example, such nucleic acid can be isolated through amplifying the nucleic acid before analysis. Amplification techniques are known to those of ordinary skill in the art and include, but are not limited to, cloning, polymerase chain reaction (PCR), polymerase chain reaction of specific alleles (PASA), polymerase chain ligation, nested polymerase chain reaction, and so forth.

The technique of hybridising labelled polynucleotide probes to polynucleotides immobilised on solid supports such as nitrocellulose filters or nylon membranes, can also be used to screen genomic or cDNA samples. Similarly, probes may be coupled to beads and hybridised to the target sequence. Isolation can be effected using known art protocols such as magnetic separation. Exemplary stringent hybridisation and wash conditions are given above.

Preferably, the detection step comprises amplifying at least the part of the nucleic acid sequence encoding the SLCO1B1 gene that contains the one or more polymorphisms, and identifying the nucleotide present in at least one allele of the polymorphism(s) encoded by said amplified DNA. Preferably the detection step comprises amplifying exon 6 of the SLCO1B1 gene comprising the SNP rs4149056, more preferably amplifying a nucleic acid sequence containing the nucleotide at position 521 of the SLCO1B1 gene and identifying the nucleotide present in at least one allele at that position.

In other embodiments, the detection step may alternatively, or additionally, comprise amplifying at least the part of the nucleic acid sequence encoding the SLCO1B1 gene that contains the one or more polymorphisms in close linkage to the SNP rs4149056, including but not limited to at least the part of intron 8 of the SLCO1B1 gene that comprises the SNPs rs1871395 or rs12317268; at least the part of intron 11 of the SLCO1B1 gene that comprises the SNPs rs4363657, rs2900478 or rs4149100; at least the part of intron 14 of the SLCO1B1 gene that comprises the SNPs rs4149081, rs11045879, rs7969341, rs11045885, rs12369881, rs12366582; and identifying the nucleotide present in at least one allele of the one or more polymorphisms encoded by said amplified DNA.

In some embodiments, the present invention may also comprise the step of amplifying a nucleic acid sequence in the biological sample from the individual that contains one or more additional SNPs that may provide independent information about myopathy risk, including but not limited to exon 5 of the SLCO1B1 gene that comprises the SNPs rs2306283, or rs11045819; or at least the part of exon 15 of the SLCO1B1 gene that comprises the SNP rs34671512.

Many variations of the basic amplification protocol are well known to the skilled technician. PCR-based detection means may include multiplex amplification of a plurality of markers simultaneously. For example, PCR primers can be selected to generate PCR products that do not overlap in size and can be analysed simultaneously. Alternatively, it is possible to amplify different genetic markers with primers that are differentially labelled and thus can each be differentially detected in the same reaction. Other techniques are known in the art to allow multiplex analysis of a plurality of markers.

The nucleotide present in at least one allele of the polymorphism in the test nucleic acid or amplification product may be detected or assayed in a variety of ways, including but not limited to size analysis, detecting specific tagged oligonucleotide primers in the reaction products, allele specific oligonucleotide (ASO) hybridisation, allele specific S1 exonuclease detection, sequencing, nucleic acid hybridisation and so forth. For example, said detecting may comprise sequencing the nucleic acid encoding the polymorphism to determine the allele or alleles present. Alternatively, the detecting may comprise the step of hybridising the product of the amplification step with a probe that is adapted to bind to one of the alleles of the genetic polymorphism.

Preferably the hybridisation probe is a detectably labelled probe. Detectable labels such as radioisotopes, enzymatic, fluorescent, chemiluminescent and bioluminescent labels may be used to facilitate detection. Labelling and visualisation of labelled probes can be carried out according to known art methods.

For convenience the hybridisation probe may be immobilised on a solid phase support including resins (such as polyacrylamides), carbohydrates (such as sepharose), plastics (such as polycarbonate), and latex beads.

In a preferred embodiment of the invention, several probes capable of hybridising specifically to allelic variants may be attached to a solid phase support. Oligonucleotides can be bound to a solid support by a variety of processes, including lithography. For example chips can hold at least 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244 and in Kozal et al. (1996) Nature Medicine 2:753. In one embodiment, a chip comprises all the allelic variants of at least one polymorphic region of a gene. The solid phase support is then contacted with a test nucleic acid and hybridisation to the specific probes is detected. Accordingly, the identity of numerous allelic variants of one or more genes can be identified in a simple hybridization experiment. For example, the identity of the allelic variant of the nucleotide polymorphism at SNP rs4149056 and/or one or more polymorphisms in close linkage with rs4149056 or other possible polymorphic regions in the SLCO1B1 gene can be determined in a single hybridisation experiment.

Suitable oligonucleotides for amplifying and sequencing the specific exons and introns of the SLCO1B1 gene are shown in Table 4 below and are provided as SEQ ID NOs: 1-51.

In some embodiments, the detecting may comprises a step of probing the test nucleic acid or the product of the amplification step with a first probe which is adapted to bind to one of the alleles of the genetic polymorphism, and preferably, probing with a second probe which is adapted to bind to the other of the alleles of the genetic polymorphism. The probes are preferably nucleic acid sequences designed to bind to one of the alleles. If one of the probes binds to the amplification product, the subject is homozygous for that allele. If however both probes bind to the amplification product, the subject if heterozygous for each allele.

In a further aspect, the invention provides a method of determining a suitable dosage for an individual in need of treatment with a statin, comprising
i) determining whether the genotype of the individual is heterozygous or homozygous for one or more polymorphisms in the SLCO1B1 gene in a biological sample from an individual; and
ii) determining a suitable dose of a statin by reference to the genotype of the one or more polymorphisms of the individual, whereby a standard dose of a statin is suitable for an individual with a heterozygous or homozygous high-risk genotype and a higher dose is suitable for an individual with a homozygous low-risk genotype.

In a further aspect, the invention provides a method of treating an individual in need of treatment with a statin, comprising:
i) determining whether the genotype of the individual is heterozygous or homozygous for one or more polymorphisms in the SLCO1B1 gene in a biological sample from an individual;
ii) classifying the individual according to their genotype at the one or more polymorphisms as determined in step i); and
iii) administering a suitable dose of a statin, whereby a standard dose of a statin is suitable for an individual with a high-risk genotype, and a higher dose is suitable for an individual with a homozygous low-risk genotype.

Preferably, the methods of the invention involve determining a suitable statin and a suitable dosage of that statin (i.e. a statin regimen) for a particular individual. For example, higher statin doses such as 80 mg simvastatin daily are recommended by health authorities for routine use, despite the increase in average myopathy risk. Such statin regimens may be suitable for individuals that do not the "high-risk" C allele of the SNP rs4149056 that is associated with statin-induced myopathy. For an individual that carries the "high-risk" C allele, a statin regimen that comprises a standard dose of a more potent statin may provide a similar level of LDL-cholesterol reduction, without the increase in myopathy risk associated with the higher statin dose.

In preferred embodiments, the methods of the invention comprise determining the genotype of the individual at the SNP rs4149056, wherein a high-risk genotype is defined as a CC or TC genotype, and a low-risk genotype is defined as a TT genotype.

In other embodiments, the methods of the invention may alternatively, or additionally, involve determining the genotype of the individual at the SNPs rs1871395, rs12317268, rs7969341, rs11045885 or rs12366582, wherein a high-risk genotype is defined as a GG or GA genotype, and a low-risk genotype is defined as a AA genotype.

In other embodiments, the methods of the invention may alternatively, or additionally, involve determining the genotype of the individual at the SNPs rs4149081 or rs 12369881, wherein a high-risk genotype is defined as a AA or AG genotype, and a low-risk genotype is defined as a GG genotype.

In other embodiments, the methods of the invention may alternatively, or additionally, involve determining the genotype of the individual at the SNPs rs4363657 or rs11045879, wherein a high-risk genotype is defined as a CC or CT genotype, and a low-risk genotype is defined as a TT genotype.

In other embodiments, the methods of the invention may alternatively, or additionally, involve determining the genotype of the individual at the SNP rs2900478, wherein a high-risk genotype is defined as a AA or AT genotype, and a low-risk genotype is defined as a TT genotype.

In other embodiments, the methods of the invention may alternatively, or additionally, involve determining the genotype of the individual at the SNP rs4149100, wherein a high-risk genotype is defined as a genotype that is homozygous for a deletion or heterozygous for a deletion; and a low-risk genotype is defined as a AA genotype.

In a further aspect, the invention provides a method of treating an individual in need of treatment with a statin, comprising
i) determining whether the genotype of the individual is heterozygous or homozygous for a cytosine (C) or a thymine (T) at the SNP rs4149056 in the SLCO1B1 gene in a biological sample from an individual;
ii) classifying the individual according to their genotype at rs4149056 determined in step i); and
iii) administering a suitable dose of a statin, whereby a standard dose of a statin is suitable for an individual with a CC or TC genotype and a higher dose is suitable for an individual with a TT genotype.

The methods of the invention may additionally involve determining a suitable statin regimen (i.e. drug and dosage), or administering a dose of a statin, for or to an individual having an elevated risk of myopathy, wherein the statin is to be used in combination with one or more alternative LDL lowering therapies.

Kits are preferably used to carry out the methods of the invention.

Accordingly, a further aspect the invention provides an in-vitro diagnostic kit for screening for susceptibility of an individual to statin-induced myopathy, comprising one or more reagents for detecting the presence or absence of one or more polymorphisms in the SLCO1B1 gene in a biological sample from an individual.

Preferably, the kits of the invention comprise one or more reagents for detecting the presence or absence of "high-risk" alleles of one or more polymorphisms that are associated with increased risk of statin-induced myopathy, and/or the presence or absence of "low-risk" alleles of the one or more polymorphisms that are associated with decreased risk of statin-induced myopathy.

Preferably, the kit comprises DNA sampling reagents and, preferably, PCR amplification reagents. Preferably, the PCR amplification reagents comprise Taq Polymerase Preferably, the one or more reagents comprise one or more allele-specific amplification primers or allele-specific probes.

Preferably, the one or more reagents comprise allele-specific amplification primers or allele-specific probes capable of determining whether the genotype of the individual is heterozygous or homozygous for the one or more polymorphisms described in detail above, more preferably for a cytosine (C) or a thymine (T) at the SNP rs4149056.

The kit will also conveniently include a control reagent (positive and/or negative) and/or a means for detecting the nucleic acid. Most usually, the kits will be formatted for assays known in the art, and more usually for PCR, Northern hybridisation or Southern ELISA assays, as are known in the art.

Preferably, the kit comprises means for probing the product of the amplification step to determine the genotype of the individual being tested. The kit preferably comprises a first probe which is adapted to bind to one of the alleles of the genetic polymorphism, and preferably, a second probe which is adapted to bind to the other of the alleles of the genetic polymorphism. The probes are preferably nucleic acid sequences designed to bind to one of the alleles. Preferably the probes are detectably labelled probes as discussed above.

The probes may be bound to a solid matrix as discussed above or packaged with reagents for binding them to the matrix. The solid matrix or substrate may be in the form of beads, plates, tubes, dip sticks, strips or biochips. Biochips or plates with addressable locating and discreet microtitre plates are particularly useful.

The kit will be comprised of one or more containers and may also include sampling equipment, for example, bottles, bags (such as intravenous fluid bags), vials, syringes, and test tubes. Other components may include needles, diluents, wash reagents and buffers. Usefully, the kit may include at least one container comprising a pharmaceutically-acceptable buffer, such as phosphate-buffered saline, Ringer's solution and dextrose solution.

Preferably, the kits comprise instructions for amplification and/or detection of the alleles of the one or more polymorphisms in the SLCO1B1 gene.

Preferably, the kits comprise instructions which define a suitable dosage for statin treatment by reference to whether the genotype of the individual is heterozygous or homozygous for the one or more polymorphisms, whereby a standard dose of a statin is suitable for an individual with a heterozygous or homozygous high-risk genotype, and a higher dose is suitable for an individual with a homozygous low-risk genotype.

In preferred embodiments the methods of the present invention comprise the additional step of obtaining a biological sample from an individual.

The methods of the invention can be used for determining a suitable statin regimen (i.e. drug and dosage) for an individual in need of treatment with a statin, wherein the individual has an increased risk of myopathy, for example through the need for a large LDL-cholesterol reduction supporting the use of higher doses of a statin, the concomitant use of certain drugs such as amiodarone, cyclosporine or gemfibrozil that slow statin clearance, or through the decreased hepatic uptake or renal clearance of statins due to genetic variants or disease. In such situations, genotyping of variants in the SLCO1B1 gene may indicate that a particular dose of a particular statin is not appropriate due to the elevated risk of myopathy. For example, for individuals that have a heterozygous or homozygous genotype for those SNPs associated with increased myopathy risk, it might be appropriate not to use a high-dose regimen of a particular statin. This may then lead to the choice of a different statin and/or statin dose and/or the addition of other LDL-cholesterol lowering therapy and/or other interventions to reduce cardiovascular risk whilst minimising the risk of myopathy.

The screening of genetic variants should thus allow the full potential benefits of statin therapy to be obtained more safely. The detection of these genetic variants may also be relevant to the effects of drugs in classes other than the statins that are transported by SLCO1B1 (such as the oral hypoglycaemic agent repaglinide).

In one embodiment the statin is selected from the list comprising lovastatin, simvastatin, pravastatin, fluvastatin, atorvastatin, pitavastatin and rosuvastatin. In preferred embodiments the statin is simvastatin, wherein a standard dose is 20 or 40 mg daily, and a higher dose is 80 mg daily.

A standard dose may be defined as the daily dosage of statin required to reduce LDL cholesterol by 30-45%. Standard doses for the other statins are typically about 10-20 mg of atorvastatin, 40-80 mg for fluvastatin, 40 mg for lovastatin, 40 mg for pravastatin, 2 mg for pitavastatin and 10 mg for rosuvastatin. A higher dose may be defined as a two-fold or higher increase in the standard daily dosage of a statin.

In some ethnic patient groups, it is expected that the daily dosage of each statin required to reduce LDL cholesterol by 30-45%, i.e., a "standard dose", will be lower than the standard doses described above. A "higher dose" will also be correspondingly lower. For example, pharmacokinetic studies conducted in the United States have demonstrated an approximate 2-fold elevation in median exposure of rosuvastatin in Asian subjects (having either Filipino, Chinese, Japanese, Korean, Vietnamese, or Asian-Indian origin) compared with a White (Caucasian) control group.[16] In such patient populations, a "standard" and "higher" dose of a particular statin may comprise a two-fold or greater decrease in the respective daily dosage of the statins described above.

As described above, the present invention is based on the identification that polymorphisms in the SLCO1B1 gene, particularly the single nucleotide polymorphism (SNP) rs4149056 or one or more polymorphisms in close linkage with rs4149056, including but not limited to rs4363657 are strongly associated (unadjusted $p=4\times10^{-9}$) with myopathy. Variation at the rs4363657 SNP variant does not affect coding of the gene, but the encoded protein is altered by the rs4149056 (Val174Ala) SNP which is in near complete linkage with SNP rs4363657 ($r^2=0.97$).

As set out in more detail in the Examples below, the frequency among controls of the C allele of the non-coding rs4363657 SNP was 0.13 and the odds ratio for myopathy was 4.3 (95% CI 2.5-7.2) per C allele and 17.4 (4.8-62.9) for CC vs. TT homozygotes. The frequency of the C allele of the coding rs4149056 SNP (Val174Ala) among controls was 0.13 and the odds ratio for myopathy was 4.5 (95% CI 2.6-7.7) per C allele and 16.9 (4.7-61.1) for CC vs. TT homozygotes.

Figure 4:
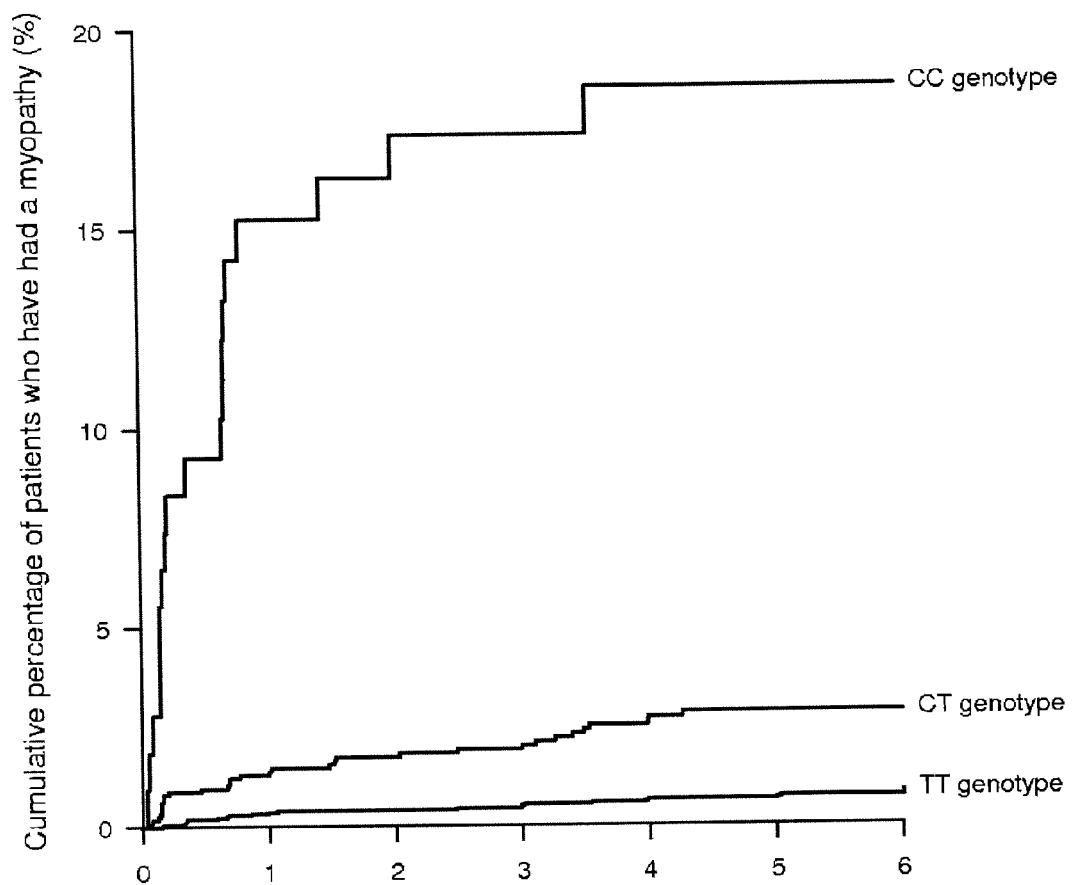
FIG. 4 shows the estimated cumulative myopathy risk by SLCO1B1 rs4149056 genotype in participants allocated 80 mg simvastatin daily.

The estimated cumulative myopathy risk by rs4149056 genotype in participants allocated 80 mg simvastatin daily is shown in FIG. 4. CC homozygotes had an 18% cumulative risk of myopathy, whereas the CT genotype was associated with a cumulative risk about 3% and the TT homozygotes had a cumulative risk of only 0.6%. This indicates that 63% of the myopathy cases in the first year and 60% of all of the myopathy cases could be attributed to rs4149056 C variant in the SLCO1B1 gene.

Other variants in the SLCO1B1 gene were studied that altered the encoded protein. Three were found to be relatively common and only in moderate linkage disequilibrium with rs4149056, indicating that they provide independent information. After taking account of the effect of rs4149056, the more common variants of the rs2306283 and rs34671512 functional SNPs were associated with higher rates of statin-induced myopathy which were statistically significant for rs2306283 and of borderline statistical significance for rs34671512. Some of these SNPs in SLCO1B1 (including, but not limited to, rs4149056) also produced modifications in the cholesterol-lowering effect of statin therapy. The susceptibility of an individual to statin-induced myopathy that can be attributed to variation in the SLCO1B1 gene is thus the cumulative risk that is produced by the combination of the effects of polymorphisms in the SLCO1B1 gene.

As discussed above, several small studies had previously considered the direct relevance to possible statin-related muscle side-effects of various candidate genes, such as CYP3A4 which is involved in the metabolism of certain statins,[13] genes involved in ubiquinone (coenzyme $Q_{10}$) deficiency,[14] and genes encoding organic anion transporting polypeptides (OATP).[11] Associations for myopathy, myalgia or statin intolerance had been reported at "nominal" p<0.05 (i.e. before making allowance for the large number of candidate genes and SNPs that were considered) with six genes individually. In the SEARCH study that is the basis of this application, there were four genes (ABCB1/MDR1, COQ2, HTR3B and HTR7) for which the inventors' large scale study did not confirm the putative associations with statistical confidence, in addition to a fifth gene, CYP2D6, that was not well covered by the genome-screen (Supplementary Tables 2, 4 and 5 in [4]).

By contrast, the comparatively large numbers of cases of statin-related myopathy among patients who were taking a high dose of simvastatin in the SEARCH study and of well-matched controls from the same population, along with independent replication in the separate large Heart Protection Study (HPS) population (as published in [4], which is hereby incorporated by reference), has demonstrated unequivocally that variation in a single gene (at rs4149056 in SLCO1B1) accounts for most cases of statin-induced myopathy.

The associations between rs4149056 genotypes and statin pharmacokinetics in previously published reports of clinical studies have been summarised by the present inventors (Supplementary Table 6 in [4]), and are shown by type of statin in Table 1 below. The association is statistically significant for each statin separately, with the exception of fluvastatin (for which there is only one study).

Evidence of previous studies showing that the SLCO1B1 rs4149056 C allele produces moderate increases in the plasma levels of several different statins supports extrapolation that rs4149056 may not only influence the risk of myopathy with simvastatin but with several other statins as well.

TABLE 1

Summary estimates by statin type of in vivo studies of the association between statin concentrations and SLCO1B1 rs4149056 SNP.

| Statin | Number of populations studied | % higher AUC per C allele among studies of this statin |
|---|---|---|
| Pravastatin (acid) | 5 | 35 (17, 56) |
| Rosuvastatin (acid) | 5 | 31 (15, 42) |
| Pitavastatin (acid) | 1 | 37 (10, 71) |
| Simvastatin acid | 1 | 61 (30, 100) |
| Atorvastatin (acid) | 1 | 54 (24, 92) |
| Fluvastatin (acid) | 1 | 10 (−9, 34) |
| Overall statin acids | 14 | 35 (26, 45) |

Heterogeneity between 6 statin groups, $\chi_5^2 = 8.55$, $p = 0.13$

The invention will now be illustrated in a non-limiting way by reference to the following Examples.

EXAMPLES

The SEARCH (Study of the Effectiveness of Additional Reductions in Cholesterol and Homocysteine) trial among 12,064 participants with a history of myocardial infarction aimed to show whether allocation to 80 mg simvastatin daily for about 7 years safely produces greater reductions in cardiovascular risk than allocation to a standard 20 mg simvastatin daily regimen.[17]

During an average follow-up of about 6 years among the 6031 participants allocated 80 mg simvastatin daily in SEARCH, 49 definite cases of myopathy had occurred and a further 49 participants were identified as having incipient myopathy (see Methods). More than half of these 98 cases of definite or incipient myopathy arose during the first year of follow-up. The mechanisms by which statins cause myopathy remain unknown, but they appear to be related to statin concentrations in the blood. Interim safety analyses in SEARCH revealed a strong, but previously unrecognised, association between the use of amiodarone and myopathy among the participants allocated 80 mg simvastatin daily, with a relative risk for myopathy of nearly 10. As a consequence, all participants taking amiodarone in SEARCH were provided with 20 mg simvastatin daily (irrespective of their original allocation), and the concomitant use of amiodarone is now contraindicated with higher simvastatin doses. It was hypothesised that similarly strong associations might exist between statin-induced myopathy on high-dose statin therapy and genetic variants, especially those that affect blood levels of statins.

Methods

Participants and Samples in SEARCH

In SEARCH, 12,064 myocardial infarction survivors aged between 18 and 80 years were randomly allocated to receive 80 mg simvastatin daily versus 20 mg simvastatin daily.[17] Exclusion criteria at the screening visit included blood creatine kinase (CK) levels above 3× the upper limit of normal (ULN; which is 250 IU/L) for the coordinating centre laboratory, blood alanine transaminse (ALT) levels above 1.5× ULN, and concomitant use of drugs that increase the risk of myopathy (i.e. fibrates, high-dose niacin, cyclosporine, nefazodone, methotrexate, and systemic azole antifungals or macrolide antibiotics). After randomisation, follow-up of participants was scheduled to occur at 2, 4, 8 and 12 months, and then at 6-monthly intervals. Information was sought about any possible myocardial infarction, hospitalisation for angina, stroke, vascular procedure, pulmonary embolus, cancer or other serious adverse experience. In addition, any new unexplained muscle pain or weakness was explicitly sought and recorded. A blood sample was taken at each follow-up visit for central laboratory assay of CK and ALT.

After an average of six years follow up, 49 of the 6031 participants allocated 80 mg simvastatin daily had developed "definite" myopathy (defined as muscle symptoms with CK>10×ULN). A further 49 participants were considered to have "incipient" myopathy based on their safety blood profile (i.e. CK>both 3×ULN and 5× screening value plus ALT >1.7× screening value, but without raised ALT alone observed), irrespective of whether or not muscle symptoms were reported. All of these 49 definite cases and 48 of the 49 incipient cases were compliant with their allocated 80 mg simvastatin daily when the diagnosis was made. By contrast, among the 6033 participants allocated 20 mg simvastatin daily, only 2 definite cases and 6 incipient cases of myopathy were identified.

The genome-wide association study was restricted to the 96 participants diagnosed with definite or incipient myopathy while taking 80 mg simvastatin daily and for whom buffy coat samples were available. Among the remaining participants who were assigned to take 80 mg simvastatin daily, 96 controls with a buffy sample were selected with matching for sex, age, estimated glomerular filtration rate and amiodarone use at baseline. These cases and controls were not known to be related, and all except one case (who was excluded from the main analyses) classified themselves as Caucasian.

Genotyping, Sequencing and Imputation in SEARCH

Frozen buffy coat samples were sent from the coordinating centre in Oxford to the Centre National de Genotypage (CNG) in Paris, France. At the CNG, DNA was extracted, its concentration was measured by fluorescence (Picogreen method) and its quality was examined by gel and PCR amplification of 2 microsatellite markers. Adequate DNA for genotyping was obtained for 85 (90%) of the 96 cases and for 90 (94%) of the 96 controls. SNP genotyping was performed with the commercial release of the Sentrix HumanHap300-Duo BeadChip (Illumina),[18] which involves a panel of 318, 237 tag SNPs derived from International HapMap resource data that is intended to capture common variation (>5%) in the genome.[19] The genotype was successfully called for >95% of the SNPs in all cases and controls, so no cases or controls were excluded from the main analysis. Multi-dimensional scaling[20] was used to detect individuals with different ancestry or other outliers: five cases clustered away from the remaining cases and the controls, indicating that they might have different ancestry (data not shown). Given the small number of participants and the strength of the putative association, those participants (except the one of known non-Caucasian origin: see above) were retained in the main analyses (but sensitivity analyses were performed with them excluded).

The main analyses included 316,184 (99.4%) of the 318,237 SNPs in the Illumina panel, with exclusion of 1098 SNPs not successfully genotyped in any samples, 139 that were monomorphic in this population, 813 that were missing in >10% of participants, and 3 that deviated among controls from Hardy-Weinberg equilibrium (HWE $p<1.6\times10^{-7}$; Bonferroni-corrected $p<0.05$). It did not appear necessary to adjust the associations of these SNPs with myopathy for genomic control, whereby extra variance in the test statistics is attributed to population substructure:[21] chi-squared values for the comparison of the observed value for each SNP versus its expected value given rank order followed the expected distribution, and the median of the 316,184 chi-squared test statistics divided by the expected median chi-squared value in null SNPs was not statistically different from 1.0 (see Results).

Following the genome-wide analysis, exons within the SLCO1B1 gene were resequenced in 83 cases and 89 controls with sufficient DNA: an additional 38 genotyped and 141 imputed[21] variants (using HapMap CEU as a reference population) with non-zero minor allele frequency were included in the case-control analysis. The Illumina panel does not cover variation in the CYP3A4 gene, which is a plausible candidate for statin-induced myopathy, so it too was resequenced in 54 cases and 62 controls with sufficient DNA: 20 (67%) of the 30 variants identified met the quality control inclusion criterion for the case-control analyses, and 11 more imputed SNPs were also included. Resequencing of the SLCO1B1 and CYP3A4 genes was performed using PCR amplicons generated by PRIMER3 to cover the whole set of exons and parts of the introns (15 fragments for SLCO1B1 and 18 fragments for CYP3A4). The oligonucleotides used for amplifying and sequencing the SLCO1B1 gene are shown in Table 4 below. PCR was undertaken in 8-uL reaction volumes using 1 unit of Taq DNA polymerase (Abgene, Epsom, UK) and 20 ng of genomic DNA. PCR products were purified using Bio-gel® P100 Gel (Bio-Rad Inc, Hercules, Calif., USA) and sequenced using the Bigdye Terminator cycle sequencing chemistry method (Applied Biosystems, Palo Alto, Calif., USA). Reactions were purified using Sephadex™ G-50 Superfine (Amersham Biosciences, Uppsala, Sweden) before applying the products to ABI 3730 DNA analysers. Detection of genetic variants was performed with in-house software (Genalys program; available at http://www.eng.fr).

Replication in the Heart Protection Study

Between July 1994 and May 1997, a total of 20,536 patients in the United Kingdom with pre-existing occlusive vascular disease or diabetes were randomised to receive either 40 mg of simvastatin daily or placebo as part of the Heart Protection Study (UPS)[22]. At each follow-up assessment (at 4, 8 and 12 months, and then every 6 months), participants were questioned about any new unexplained muscle pain or weakness, and blood was taken at each follow-up visit for central laboratory assay of CK and ALT. During 5 years average follow-up, 24 myopathy cases (10 definite plus 14 incipient; 23 while taking statin) were identified among 10,269 participants allocated 40 mg simvastatin daily versus 12 cases (4 definite plus 8 incipient; 3 while taking statin) among 10,267 allocated placebo. Using DNA extracted from 19,856 (97%) participants, the rs4149056 and rs2306283 SNPs in SLCO1B1 were successfully genotyped in 16,664 participants classified as Caucasian. Effects of these genotypes on myopathy risk and on LDL-cholesterol reduction were then assessed.

Statistical Analysis and Software

Standard 1d.f. (trend) and 2 d.f. (genotypic) tests of association with genotype and case-control odds ratios for myopathy from logistic regressions were calculated using SAS and PLINK (v.1.00).[23] For the genome-wide comparisons, uncorrected p-values for each separate SNP that were smaller than $5\times10^{-7}$ were considered to be strong evidence for association, while those between $5\times10^{-5}$ and $5\times10^{-7}$ were considered to provide moderate evidence (see Wellcome Trust Case-Control Consortium report for a rationale[24]). Haploview v4.0 release candidate 2[25] was used to estimate linkage disequilibrium and plot association results for genotyped SNPs. Haplotype frequencies and associated risks were estimated using tools in the haplo.stats (v1.3.1) package[26] in R (v2.6.1)[27]. Physical positions refer to NCBI build-36 of the human genome, and alleles are expressed in the forward strand of the reference human genome (NCBI build-36). Ensembl version 46 and NCBI dbSNP build 127 and published reports[11,28,29] were used to classify SNPs as synonymous or non-synonymous and to identify their location within introns or exons. The attributable risk of myopathy with 80 mg simvastatin daily was estimated by a life-table analysis in which censoring at death or at termination of the study simvastatin prescription prior to myopathy was taken to be independent of genotype. Participants on amiodarone at baseline were excluded from this analysis because their simvastatin dose was reduced early in the trial (chiefly during the first year of follow-up) due to a high risk of myopathy.

Results

Participant Characteristics

As had been observed previously in the SEARCH study,[30] concomitant use of amiodarone increased the risk of myopathy among participants allocated 80 mg simvastatin daily, with a relative risk of 8.8 (95% CI 4.2 to 18.4) during the first year of follow-up. After detecting this association early in the trial, all participants taking amiodarone were provided with 20 mg simvastatin daily (irrespective of their original allocation), which may explain the less extreme relative risk observed subsequently. Modest increases in the risk of myopathy with 80 mg simvastatin daily were observed among older participants, among women (who tended to be older due to trial eligibility requiring previous myocardial infarction), among those with evidence of impaired renal function, and among those taking calcium channel blockers at baseline.

Genome-Wide Association Study

The genome-wide association study involved 85 suspected myopathy cases and 90 controls, all of whom had been taking 80 mg simvastatin daily in SEARCH. Single SNP analysis yielded one strong association with myopathy (uncorrected $p=4\times10^{-9}$; Bonferroni-corrected $p<0.001$) for the non-coding rs4363657 SNP located within intron 11-12 of the SLCO1B1 gene on chromosome 12 (with no SNPs in any other region yielding an uncorrected $p<10^{-5}$: FIG. 1). The rs4363657 C allele prevalence was 0.13 among the controls, with odds ratios for myopathy of 4.3 (95% CI 2.5-7.2) per C allele and 17.4 (4.8-62.9) for CC vs. TT homozygotes.

Figure 2:
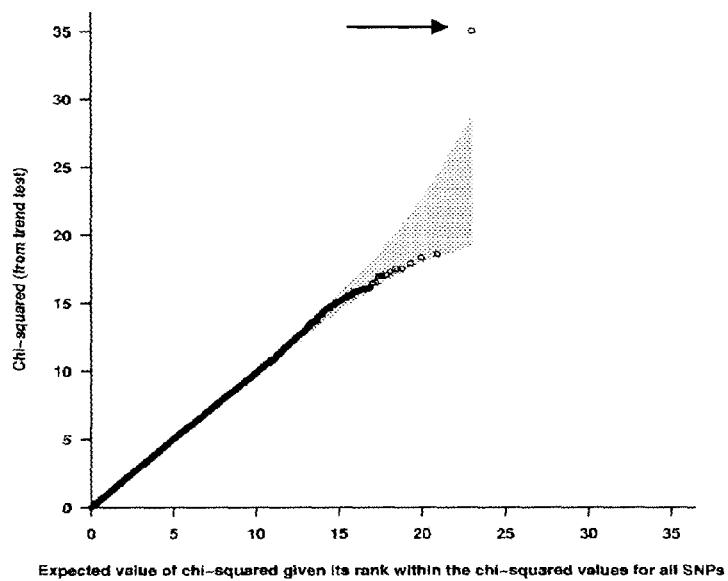
FIG. 2 shows chi-squared values for each measured SNP versus expected value given rank (quantile-quantile plot) in the genome-wide association study. The solid and dotted lines show the expected distribution and 95% confidence interval (CI) respectively under the null hypothesis of no association at any locus. The arrow indicates the SNP rs4363657 which is located within intron 11 of the SLCO1B1 gene on chromosome 12.

There was little evidence of deviation from Hardy-Weinberg equilibrium. Nor did the results appear to be materially affected by population substructure or other potential sources of systematic deviation: the chi-squared value for rs4363657 was well outside the 95% confidence interval of the quantile-quantile plot, whereas values for all of the other genotyped SNPs were within this confidence interval (FIG. 2).

Candidate Genotyping and Haplotype Analysis

In light of this strong association of myopathy with rs4363657, additional SNPs within SLCO1B1 (+/−10 kb) were genotyped by resequencing or imputed from genotyped SNPs. Of these, two genotyped (and nine imputed) SNPs were in nearly complete linkage disequilibrium with rs4363657 (each $r^2$>0.95). But, among them, only rs4149056 (Val174Ala) in exon 6 was "non-synonymous" (i.e. altered the encoded protein): the prevalence of its C allele was 0.13 among controls, with odds ratios for myopathy of 4.5 (2.6-7.7) per C allele and 16.9 (4.7-61.1) for CC vs. TT homozygotes ($p=2\times10^{-9}$; four missing results imputed). These data are summarised in Table 2 below.

with different ancestry or other outliers[20]: excluding the 4 participants who appeared to cluster away from the remaining cases and controls only changed the p-value for rs4149056 from $2.4\times10^{-9}$ to $2.0\times10^{-9}$ (and did not alter the genomic regions classified as strongly significant).

Attributable Risk of Myopathy

The controls had been selected on the basis of not having developed myopathy and, hence, there was a lower probability that they had the higher-risk rs4149056 allele. After allowing for this selection bias, the population prevalence of the C allele was estimated to be 0.146 (consistent with the 0.14-0.22 range found previously among Caucasians[28]). Based on this prevalence, a life-table analysis was used to estimate the cumulative myopathy risk among participants taking 80 mg simvastatin daily according to their rs4149056 genotype (FIG. 4). CC homozygotes had an 18% cumulative risk, chiefly occurring during the first year, while the CT genotype was associated with a cumulative risk of about 3%. By contrast, the cumulative risk of myopathy was only 0.6% among TT homozygotes taking 80 mg simvastatin. Overall, more than 60% of these myopathy cases could be attributed to the rs4149056 C variant in the SLCO1B1 gene. These data are summarised in Table 3 below.

TABLE 2

Single nucleotide polymorphisms strongly associated with myopathy.

| SNP | Position | Trend P value | Genotypic P value | Risk allele | Other allele | Risk Allele Frequency Case | Risk Allele Frequency Control |
|---|---|---|---|---|---|---|---|
| rs4363657 | 21259989 | $4.1 \times 10^{-9}$ | $2.5 \times 10^{-8}$ | C | T | 0.46 | 0.13 |
| rs4149056 | 21222816 | $2.4 \times 10^{-9}$ | $1.1 \times 10^{-8}$ | C | T | 0.45 | 0.13 |

| SNP | Position | HWE P value in controls | OR (95% CI) per risk allele | Heterozygote OR | Homozygote OR | Gene and amino acid change if non-synonymous |
|---|---|---|---|---|---|---|
| rs4363657 | 21259989 | $1.8 \times 10^{-1}$ | 4.3 (2.5-7.2) | 4.4 | 17.4 | SLCO1B1 |
| rs4149056 | 21222816 | $1.5 \times 10^{-1}$ | 4.5 (2.6-7.7) | 5.0 | 16.9 | SLCO1B1: Val > Ala |

Five other non-synonymous variants were found within, SLCO1B1, including three that were relatively common: rs2306283 (44% G allele frequency in controls), rs11045819 (18% A allele frequency) and rs34671512 (8% C allele frequency). There was only moderate linkage disequilibrium between rs4149056 and these three variants (each pairwise $r^2$<0.20). In haplotypes with rs4149056, both the rs2306283 G allele and rs34671512 C allele were associated with borderline significant (p=0.03 and p=0.06, respectively) lower risks of myopathy and thus may provide independent information about myopathy risk, whereas rs11045819 did not appear to influence risk.

Subgroup Findings for rs4149056

Figure 3:
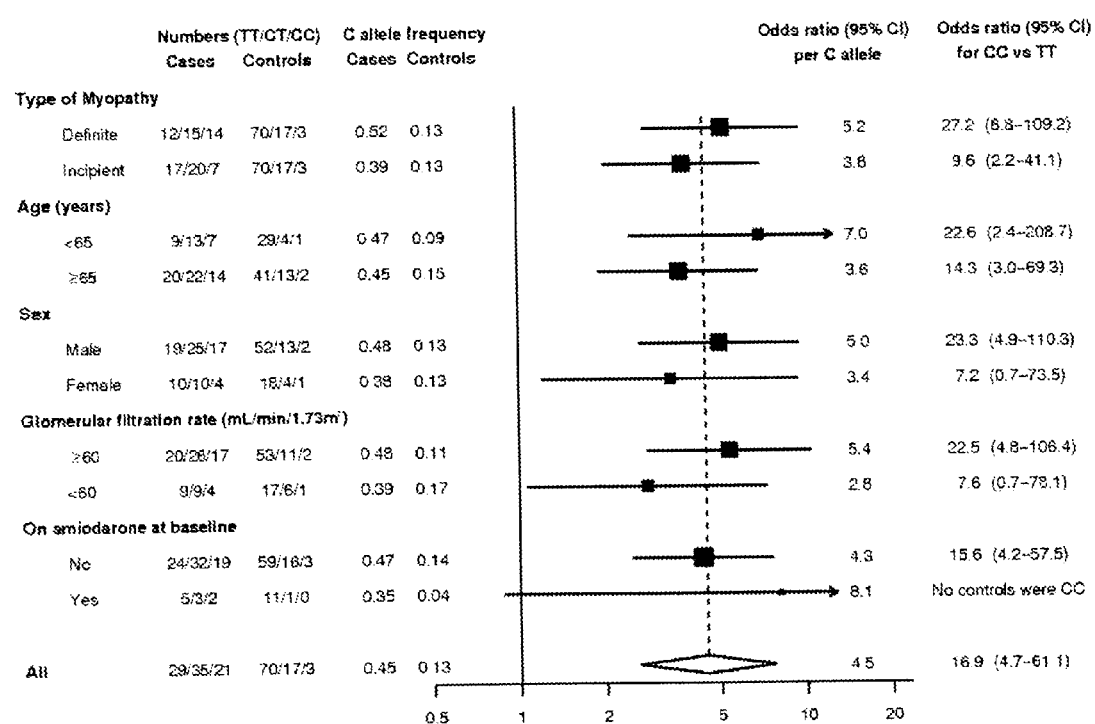
FIG. 3 shows odds ratios for myopathy associated with the rs4149056 SNP in the SLCO1B1 gene within different categories of participants. Black squares indicate odds ratios in each subdivision (with area proportional to the amount of statistical information in each subdivision) and horizontal lines indicate 95% CI (ending with an arrow head when CI extends beyond scale). The overall odds ratio and its 95% CI are indicated by an unshaded diamond.

FIG. 3 shows that the odds ratios for myopathy associated with rs4149056 were not significantly different among definite versus incipient myopathy cases or in subgroups with respect to baseline age, sex, estimated glomerular function or amiodarone use (albeit with limited power to detect modest differences). If that is the case then it implies that the effects of the genotype and the effects of these other factors (in particular amiodarone use) on myopathy risk are multiplicative (e.g. a 4-fold increase in a heterozygote for rs4149056 and a 10-fold increase with concomitant amiodarone use would translate into a 40-fold increased risk of myopathy). Multi-dimensional scaling was used to detect individuals

TABLE 3

Cumulative numbers and percentages with myopathy by genotype.

| | | Year 1 | | | |
|---|---|---|---|---|---|
| | Population | | | Attributable to genotype | |
| Genotype | frequency | N | % | N | % of total |
| TT | 0.730 | 12 | 0.34 | 0.0 | 0 |
| CT | 0.249 | 17 | 1.38 | 12.8 | 75 |
| CC | 0.021 | 16 | 15.25 | 15.6 | 98 |
| All genotypes | 1.000 | 45 | 0.91 | 28.4 | 63 |

| | | Year 5 | | | |
|---|---|---|---|---|---|
| | Population | | | Attributable to genotype | |
| Genotype | frequency | N | % | N | % of total |
| TT | 0.730 | 21 | 0.63 | 0.0 | 0 |
| CT | 0.249 | 32 | 2.83 | 24.9 | 78 |
| CC | 0.021 | 19 | 18.55 | 18.4 | 97 |
| All genotypes | 1.000 | 72 | 1.56 | 43.3 | 60 |

Replication in Heart Protection Study

Among 16,664 genotyped participants in HPS,[22] the rs4149056 and rs2306283 variants were not associated with significant differences in pre-treatment LDL-cholesterol levels. Prior to randomisation, all of these participants took 4-6 weeks of 40 mg simvastatin daily and the average reduction in LDL-cholesterol was 40.57% (SE 0.12). When both variants were considered together, the reductions were 1.28% (0.25) smaller per rs4149056 C allele (p<0.0001) and 0.62% (0.18) larger per rs2306283 G allele (p<0.0001). Overall in HPS, there were 23 definite or incipient cases of myopathy among participants who were taking their allocated 40 mg simvastatin daily compared with 9 cases among placebo-allocated participants who were not taking a statin. Consequently, by contrast with the SEARCH study, only about half of the myopathy cases among participants taking simvastatin in HPS are likely to have been statin-induced. Even so, the comparison within HPS (restricted to Caucasians) between 21 myopathy cases on 40 mg simvastatin and 16,643 genotyped controls without myopathy confirmed that the rs4149056 SNP is associated with myopathy (p=0.004), albeit with a less extreme relative risk of 2.6 (1.3-5.0) per C allele. These 17,000 genotyped participants without myopathy also provide an alternative control population for the SEARCH cases, yielding an odds ratio of 4.7 (3.5-6.4) per rs4149056 C allele and a stronger p-value of $3 \times 10^{-28}$.

Comparisons with Previous Studies

No previously published study has provided statistically conclusive evidence of associations of genetic variants with statin-induced myopathy. In a study of 8 candidate genes in 10 myopathy cases and 26 controls, an association with SLCO1B1 SNPs was reported,[15] but those results were not statistically robust after adjustment for multiple comparisons. In the present study, no significant associations were found for SNPs in any of the other genes that had previously been reported to be associated with myopathy or with statin pharmacokinetics (Supplementary Tables 2, 4 and 5 in [4]). In particular, the 20 genotyped and 11 imputed SNPs in the CYP3A4 gene (which is involved in simvastatin elimination[13]) were not significantly associated with myopathy (Supplementary Table 2b in [4]). It has been reported that 10% of statin-induced myopathy cases referred for genetic testing had, or were carriers for, one of three inherited metabolic myopathies (McArdle's disease, carnitine palmitoyltransferase II deficiency, or myoadenylate deaminase deficiency).[31] In the present study, however, there were no significant associations of myopathy with SNPs in those genes.

Discussion

The SEARCH and HPS studies provide very strong evidence that at least one common genetic variant in SLCO1B1 substantially alters the risk of statin-induced myopathy. Among patients taking 20-40 mg simvastatin daily (or standard doses of other statins), the incidence of myopathy is typically only about one per 10,000 patients per year[3] and the impact of these gene variants on the absolute risk of myopathy is likely to be small (as indicated by our results among participants in HPS). By contrast, the risk of myopathy may be increased ten-fold with 80 mg simvastatin daily or other high-dose statin regimens, as well as with concomitant use of certain drugs[31] (such as cyclosporine, gemfibrozil and, as found in SEARCH, amiodarone[30]). Hence, the use of such drugs in people taking high-dose statin regimens who have the C allele of the rs4149056 polymorphism may produce particularly high absolute risks of myopathy (as is suggested by the approximately multiplicative effects of rs4149056 genotype and amiodarone use in FIG. 3).

SLCO1B1 encodes the organic anion-transporting polypeptide OATP1B1, which mediates the hepatic uptake of various drugs, including most statins and statin acids. Several small clinical studies have investigated associations between rs4149056 SLCO1B1 genotypes and the pharmacokinetics of statin elimination (typically involving measurement of blood statin levels during a 24 hour period following administration of a single regular dose).[11] Although not all of those studies yielded statistically significant results, the collective evidence indicates that statin levels are higher in people with the C allele of this polymorphism. Five of those studies also examined haplotypes of rs4149056 and rs2306283 and, in aggregate, those studies suggest that the rs2306283 G variant is associated with lower statin concentrations (data not shown), which is consistent with the lower risk of myopathy observed in the SEARCH study. Genetic variants that slow hepatic uptake might also be expected to reduce the cholesterol-lowering effect of a statin regimen. Our data from participants in the Heart Protection Study confirmed that these variants do cause small differences in the LDL cholesterol reductions produced by simvastatin.[22]

The Illumina HumanHap300-Duo panel is estimated from HapMap CEU samples to provide about 75% genomic coverage for common SNPs (at $r^2 \geq 0.8$) in Caucasians. Given the numbers of cases and controls, the present genome-wide association study had only about 50% power to detect odds ratios of about 4 for common variants at a "strong significance" p-value of $5 \times 10^{-7}$. Hence, the existence of variants that carry a 2-4 fold higher myopathy risk cannot be ruled out by this analysis. Genes with prior evidence for links with myopathy or statin pharmacokinetics might be regarded as "candidates" that require less extreme uncorrected p-values to provide good evidence of association. Supplementary Table 5 in [4] lists approximately 100 such SNPs, which represents about 1/3000 of the genome screen; so a p-value of $1.5 \times 10^{-3}$ (i.e. 3000 times $5 \times 10^{-7}$) might be considered "significant" for these candidates. No such p-values were, however, achieved for any of the SNPs studied in these regions.

In conclusion, this genome-wide association study has successfully identified common genetic variants in the SLCO1B1 gene that are associated with substantial alterations in the risk of simvastatin-induced myopathy. These findings are likely to apply to other statins because myopathy is a class effect and SLCO1B1 polymorphisms have been shown to affect the blood levels of several statins. Moreover, these variants may be relevant to the effects of drugs in other classes that are transported by SLCO1B1 (such as the oral hypoglycaemic agent repaglinide). Genotyping of SLCO1B1 polymorphisms offers scope for tailoring the statin dose and safety monitoring (especially during the first year of treatment when the absolute risks of myopathy are greatest) in order to achieve the benefits of statin therapy more safely and effectively in the future.

TABLE 4

Oligonucleotides used for resequencing SLCO1B1 gene

| Exon number | Name | Sequence | Usage | SEQ ID No. |
|---|---|---|---|---|
| Exon1 | SLCO1B1_P001_PF | AATGGTCTTGCAGTTAATTGGG | PCR | 1 |
| | SLCO1B1_P001_PR | TCCCTTCACCCTGTATCAAACT | PCR | 2 |

TABLE 4-continued

Oligonucleotides used for resequencing SLCO1B1 gene

| Exon number | Name | Sequence | Usage | SEQ ID No. |
|---|---|---|---|---|
| | SLCO1B1_P001_SF | TGGCAACTGGAGTGAACTCTT | sequencing | 3 |
| | SLCO1B1_P001_SR | TTCCCTCTACTCCCACCCTT | sequencing | 4 |
| Exon2 | SLCO1B1_P002_PF | TCTACTCTGTGCAAGGGGCT | PCR | 5 |
| | SLCO1B1_P002_SF | TCCAGCATTGACCTAGCAGA | sequencing | 6 |
| | SLCO1B1_P002_SR | TCGTGATCAATCCAAAACCA | PCR and sequencing | 7 |
| Exon3 | SLCO1B1_P003_PF | TGTTTTTCAGCTGGCTTCCT | PCR | 8 |
| | SLCO1B1_P003_PR | GGTCTAACGTAGGTTGCTCTGAA | PCR | 9 |
| | SLCO1B1_P003_SF | AGAATGTACTGCCACTCCCCT | sequencing | 10 |
| | SLCO1B1_P003_SR | TATTGCCAAATTGCCTGTGA | sequencing | 11 |
| Exon4 | SLCO1B1_P004_PF | ATGCCATGGTTTATTCTTTTCA | PCR | 12 |
| | SLCO1B1_P004_PR | TAAGTTTCTCCCCCATGTGC | PCR | 13 |
| | SLCO1B1_P004_SF | TGTCTTTGAGGGAAGGCACT | sequencing | 14 |
| | SLCO1B1_P004_SR | GCTTCAGTGAAATGATGGGAA | sequencing | 15 |
| Exon5 | SLCO1B1_P005_PF | ATAACCCACTTAGCCTGGGG | PCR | 16 |
| | SLCO1B1_P005_PR | GCTGCCTGTGTGTTCTCAAA | PCR | 17 |
| | SLCO1B1_P005_SF | GGGGAAGATAATGGTGCAAA | sequencing | 18 |
| | SLCO1B1_P005_SR | CGGCAGGTTTATCATCCAGT | sequencing | 19 |
| Exon6 | SLCO1B1_ex6_PF | TTGTCAAAGTTTGCAAAGTG | PCR and sequencing | 20 |
| | SLCO1B1_ex6_PR | GCCAAGAATGCATGGTTCTT | PCR and sequencing | 21 |
| Exon7 | SCLO1B1_P127_PF | TTGTATGATCACTTTCCCTTGTC | PCR and sequencing | 22 |
| | SCLO1B1_P127_PR | CACATCAACATCCAAGCCAC | PCR and sequencing | 23 |
| Exon8 | SLCO1B1_P007_PF | TTCATTGCTGACCCTTTCTTG | PCR | 24 |
| | SLCO1B1_P007_PR | GCATCACCCACTAGGTTCTTG | PCR | 25 |
| | SLCO1B1_P007_SF | AGCCATCAAGTGCACACAAG | sequencing | 26 |
| | SLCO1B1_P007_SR | TTTTGTTGGTTTCTCCCTGC | sequencing | 27 |
| Exon9 | SLCO1B1_P008_PF | AAAACAGCACTTACGTATGACCC | PCR and sequencing | 28 |
| | SLCO1B1_P008_PR | TGCAACTTCAAATGCAGAGC | PCR and sequencing | 29 |
| Exon10 | SLCO1B1_P009_PF | CAAACACTGCATGTTCCCAC | PCR | 30 |
| | SLCO1B1_P009_PR | TCCATCCAAGATTACAGTGGTG | PCR | 31 |
| | SLCO1B1_P009_SF | AGCAAGGGGAGGAAGAACAT | sequencing | 32 |
| | SLCO1B1_P009_SR | TTTCTCTAAGCCTTACTTTTCCCA | sequencing | 33 |
| Exon11 | SLCO1B1_P010_PF | CAGTGAGCTGAAAGGAATGTCA | PCR | 34 |
| | SLCO1B1_P010_PR | AGGAAGTGCTGACAATGGGT | PCR | 35 |
| | SLCO1B1_P010_SF | GGCAAAGATGGAGAGCGTAA | sequencing | 36 |
| | SLCO1B1_P010_SR | AGAAAAACCTGATTGTGCCCT | sequencing | 37 |
| Exon12 | SLCO1B1_P011_PF | GGATAATTCCTCCTCAGGGC | PCR | 38 |
| | SLCO1B1_P011_PR | TGGAATGTTATCAAATGGAGCA | PCR | 39 |
| | SLCO1B1_P011_SF | TCTGCAGAGGGTAAAAGGGA | sequencing | 40 |
| | SLCO1B1_P011_SR | TACCCTGAGAGATGCAAGGC | sequencing | 41 |
| Exon13 | SCLO1B1_P151_PF | GGCCATTCAACTGTGAGCTT | PCR and sequencing | 42 |
| | SCLO1B1_P151_PR | TAGGCCCTTCACTCTGCCTA | PCR and sequencing | 43 |
| Exon14 | SLCO1B1_25 | TTGGGTAGATGCAGAACAAA | PCR and sequencing | 44 |
| | SLCO1B1_26 | TGACATGAGGAGAGTTTTGG | PCR | 45 |
| Exon15 | SLCO1B1_P014_PF | GAAGGCCAGAGGCAACTAGA | PCR | 46 |
| | SLCO1B1_P014_PR | GTGGGAAAGCTGCAAAAGAA | PCR | 47 |
| | SLCO1B1_P014_SF1 | CGTTATGCCCCAATAAAAAGAA | sequencing | 48 |
| | SLCO1B1_P014_SR1 | AGCTCCTCCTTTTTAACCTCTACC | sequencing | 49 |
| | SLCO1B1_P014_SF2 | GCTGGGGCAGATAGTGAAAC | sequencing | 50 |
| | SLCO1B1_P014_SR2 | GCGGCAAATGATCTAGGAAA | sequencing | 51 |

REFERENCE LIST

1. Cholesterol Treatment Trialists' (CTT) Collaborators. Efficacy and safety of cholesterol-lowering treatment: prospective meta-analysis of data from 90,056 participants in 14 randomised trials of statins. Lancet 2005; 366:1267-78.
2. Thompson P D, Clarkson P, Karas R H. Statin-associated myopathy. JAMA 2003; 289:1681-90.
3. Armitage J. The safety of statins in clinical practice. Lancet 2007; 370:1781-90.
4. Link E, Parish S, Armitage J, Bowman L, Heath S, Matsuda F, et al. SLCO1B1 variants and statin-induced myopathy—a genomewide study. N Engl J Med 2008; 359:789-99.
5. Corsini A, Bellosta S, Davidson M H. Pharmacokinetic interactions between statins and fibrates. Am J Cardiol 2005; 96:44 K-49K; discussion 34K-35K.

6. Law M, Rudnicka A R. Statin safety: a systematic review. Am J Cardiol 2006; 97:S52-S60
7. Ballantyne C M, Corsini A, Davidson M H, Holdaas H, Jacobson T A, Leitersdorf E, et al. Risk for myopathy with statin therapy in high-risk patients. Arch Intern Med 2003; 163:553-64.
8. Molden E. Variability in Cytochrome P450-Mediated Metabolism of Cardiovascular Drugs: Clinical Implications and Practical Attempts to Avoid Potential Problems. Heart Drug 2004; 4:55-79.
9. Simonson S G, Raza A, Martin P D, Mitchell P D, Jarcho J A, Brown C D, et al. Rosuvastatin pharmacokinetics in heart transplant recipients administered an antirejection regimen including cyclosporine. Clin Pharmacol Ther 2004; 76:167-77.
10. Mangravite L M, Thorn C F, Krauss R M. Clinical implications of pharmacogenomics of statin treatment. Pharmacogenomics J 2006; 6:360-74.
11. Konig J, Seithel A, Gradhand U, Fromm M F. Pharmacogenomics of human OATP transporters. Naunyn Schmiedebergs Arch Pharmacol 2006; 372:432-43.
12. shitara Y, Sugiyama Y. Pharmacokinetic and pharmacodynamic alterations of 3-hydroxy-3-methylglutaryl coenzyme A (HMG-CoA) reductase inhibitors: drug-drug interactions and interindividual differences in transporter and metabolic enzyme functions. Pharmacol Ther 2006; 112:71-105.
13. Kajinami K, Brousseau M E, Ordovas J M, Schaefer E J. CYP3A4 genotypes and plasma lipoprotein levels before and after treatment with atorvastatin in primary hypercholesterolemia. Am J Cardiol 2004; 93:104-7.
14. Oh J, Ban M R, Miskie B A, Pollex R L, Hegele R A. Genetic determinants of statin intolerance. Lipids Health Dis 2007; 6:7
15. Morimoto K, Ueda S, Seki N, Igawa Y, Kameyama Y, Shimizu A, et al. OATP-C(OATP01B1)*15 is associated with statin-induced myopathy in hypercholesterolemic patients. Clinical Pharmacology & Therapeutics 2005; 77:P21-P21
16. Kim K T, Birmingham B K, Azumaya C T, Chen Y, Schneck D, Zalikowski J. Increased systemic exposure to rosuvastatin in Asian subjects residing in the United States compared to Caucasian subjects. Clinical Pharmacology and Therapeutics 2008; 83:S14 Abstract.
17. SEARCH Study Collaborative Group. Study of the effectiveness of additional reductions in cholesterol and homocysteine (SEARCH): characteristics of a randomized trial among 12064 myocardial infarction survivors. Am Heart J 2007; 154:815-23.e6.
18. Gunderson K L, Kuhn K M, Steemers F J, Ng P, Murray S S, Shen R. Whole-genome genotyping of haplotype tag single nucleotide polymorphisms. Pharmacogenomics 2006; 7:641-8.
19. International HapMap Consortium. A haplotype map of the human genome. Nature 2005; 437:1299-320.
20. Price A L, Patterson N J, Plenge R M, Weinblatt M E, Shadick N A, Reich D. Principal components analysis corrects for stratification in genome-wide association studies. Nat Genet. 2006; 38:904-9.
21. Devlin B, Roeder K. Genomic control for association studies. Biometrics 1999; 55:997-1004.
22. Heart Protection Study Collaborative Group. MRC/BHF Heart Protection Study of cholesterol lowering with simvastatin in 20,536 high-risk individuals: a randomised placebo-controlled trial. Lancet 2002; 360:7-22.
23. Purcell S, Neale B, Todd-Brown K, Thomas L, Ferreira M A, Bender D, et al. PLINK: a tool set for whole-genome association and population-based linkage analyses. Am J Hum Genet. 2007; 81:559-75.
24. Wellcome Trust Case Control Consortium. Genome-wide association study of 14,000 cases of seven common diseases and 3,000 shared controls. Nature 2007; 447:661-78.
25. Barrett J C, Fry B, Maller J, Daly M J. Haploview: analysis and visualization of LD and haplotype maps. Bioinformatics 2005; 21:263-5.
26. Sinnwell J P, Schaid D J and Y u and Z. haplo.stats: Statistical Analysis of Haplotypes with Traits and Covariates when Linkage Phase is Ambiguous. R package version 1.3.1. http://mayoresearch.mayo.edu/mayo/research/schaid_lab/software.cfm.2007.
27. R Development Core Team. R: A Language and Environment for Statistical Computing. Vienna, Austria: R Foundation for Statistical Computing, 2007.
28. Pasanen M K, Backman J T, Neuvonen P J, Niemi M. Frequencies of single nucleotide polymorphisms and haplotypes of organic anion transporting polypeptide 1B1 SLCO1B1 gene in a Finnish population. Eur J Clin Pharmacol 2006; 62:409-15.
29. Tirona R G, Leake B F, Merino G, Kim R B. Polymorphisms in OATP-C: identification of multiple allelic variants associated with altered transport activity among European- and African-Americans. J Biol Chem 2001; 276:35669-75.
30. Zocor datasheet. http://www.emc.medicines.org.uk/emc/assets/c/html/DisplayDoc.asp?DocumentID=1201.2007.
31. Vladutiu G D, Simmons Z, Isackson P J, Tarnopolsky M, Peltier W L, Barboi A C, et al. Genetic risk factors associated with lipid-lowering drug-induced myopathies. Muscle Nerve 2006; 34:153-62.

The invention claimed is:

1. A method, comprising:
   (a) assaying for the presence or absence of a C or T allele for single nucleotide polymorphism rs4149056 in the SLCO1B1 gene in a biological sample obtained from a patient in need of treatment with a statin;
   (b) correlating the identity of the allele of said polymorphism with risk of statin-induced myopathy;
   (c) establishing a statin type and dosage based on said patient's statin-induced myopathy risk; and
   (d) administering said statin type and dosage to said patient.

2. The method of claim 1, wherein said assaying step comprises amplifying at least part of the SLCO1B1 gene comprising said polymorphism, and identifying the nucleotide present in at least one allele of said polymorphism in the amplified gene.

3. The method of claim 2, wherein said assaying step comprises amplifying exon 6 of the SLCO1B1 gene comprising the SNP rs4149056.

4. The method of claim 1, wherein said biological sample is selected from the group consisting of individual cells, cell populations, bodily tissues, and bodily fluids.

5. The method of claim 1, wherein, for a patient with the TT genotype, said administered statin dosage is higher than the standard dosage, and for a patient with a CC or TC genotype, said statin dosage is the standard dosage.

6. The method of claim 1, wherein said statin is lovastatin, simvastatin, pravastatin, fluvastatin, atorvastatin, pitayastatin, or rosuvastatin.

7. The method of claim 6, wherein said statin is atorvastatin or simvastatin.

8. A method comprising:
   (a) assaying for the presence of a C or T allele for single nucleotide polymorphism rs4363657 in the SLCO1B1 gene in a biological sample obtained from a patient in need of treatment with a statin;
   (b) correlating the identity of the allele of said polymorphism with risk of statininduced myopathy;
   (c) establishing a statin type and dosage based on said patient's statin-induced myopathy risk; and
   (d) administering said statin type and dosage to said patient.

9. The method of claim 8, wherein said assaying step comprises amplifying at least part of the SLCO1B1 gene comprising said polymorphism, and identifying the nucleotide present in at least one allele of said polymorphism in the amplified gene.

10. The method of claim 9, wherein said assaying step comprises amplifying intron 11 of the SLCO1B1 gene comprising the SNP rs4363657.

11. The method of claim 8, wherein said biological sample is selected from the group consisting of individual cells, cell populations, bodily tissues, and bodily fluids.

12. The method of claim 8, wherein, for a patient with the IT genotype, said administered statin dosage is higher than the standard dosage, and for a patient with a CC or IC genotype, said statin dosage is the standard dosage.

13. The method of claim 8, wherein said statin is lovastatin, simvastatin, pravastatin, fluvastatin, atorvastatin, pitavastatin, or rosuvastatin.

14. The method of claim 13, wherein said statin is atorvastatin or simvastatin.

* * * * *

UNITED STATES PATENT AND TRADEMARK OFFICE
CERTIFICATE OF CORRECTION

PATENT NO. : 8,455,194 B2
APPLICATION NO. : 13/408672
DATED : June 4, 2013
INVENTOR(S) : Emma Link et al.

Page 1 of 1

It is certified that error appears in the above-identified patent and that said Letters Patent is hereby corrected as shown below:

In the claims

At claim 12, column 44, line 58, the genotype "IT" should be changed to -TT-.

At claim 12, column 44, line 59, the genotype "IC" should be changed to -TC-.

Signed and Sealed this
Tenth Day of November, 2015

Michelle K. Lee
*Director of the United States Patent and Trademark Office*

(12) EX PARTE REEXAMINATION CERTIFICATE (10466th)
United States Patent
Link et al.

(10) Number: US 8,455,194 C1
(45) Certificate Issued: *Jan. 6, 2015

(54) DIAGNOSTIC METHODS

(75) Inventors: Emma Link, Oxford (GB); Sarah Parish, Oxford (GB); Rory Collins, Oxford (GB); Mark Lathrop, Paris (FR)

(73) Assignee: Isis Innovation Limited, Summertown, Oxford (GB)

Reexamination Request:
No. 90/013,065, Nov. 22, 2013

Reexamination Certificate for:
Patent No.: 8,455,194
Issued: Jun. 4, 2013
Appl. No.: 13/408,672
Filed: Feb. 29, 2012

(*) Notice: This patent is subject to a terminal disclaimer.

Related U.S. Application Data

(63) Continuation of application No. 12/920,297, filed as application No. PCT/GB2009/000547 on Feb. 27, 2009.

(30) Foreign Application Priority Data

Feb. 29, 2008 (GB) .................................... 0803833.3
Jul. 7, 2008 (GB) .................................... 0812414.1

(51) Int. Cl.
*C12Q 1/68* (2006.01)
*C12P 19/34* (2006.01)
*C07H 21/02* (2006.01)
*C07H 21/04* (2006.01)

(52) U.S. Cl.
CPC ........ *C12Q 1/6883* (2013.01); *C12Q 2600/172* (2013.01)
USPC ........................... 435/6.1; 435/91.1; 536/23.1

(58) Field of Classification Search
None
See application file for complete search history.

(56) References Cited

To view the complete listing of prior art documents cited during the proceeding for Reexamination Control Number 90/013,065, please refer to the USPTO's public Patent Application Information Retrieval (PAIR) system under the Display References tab.

*Primary Examiner* — Sharon Turner

(57) ABSTRACT

This invention relates to a method of determining the susceptibility of an individual to statin-induced myopathy, comprising detecting the presence or absence of one or more polymorphisms in the SLCO1B1 gene in a biological sample from an individual, whereby the presence of one or more polymorphisms indicates that the individual has altered susceptibility to statin-induced myopathy.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-2 and 5 are determined to be patentable as amended.

Claims 3-4 and 6-7, dependent on an amended claim, are determined to be patentable.

New claims 15-25 are added and determined to be patentable.

Claims 8-14 were not reexamined.

1. A method, comprising:
 (a) assaying for the presence [or absence] of a C or T allele [for] *at* single nucleotide polymorphism rs4149056 in the SLCO1B1 gene in a biological sample obtained from a patient in need of treatment with a statin;
 [(b) correlating the identity of the allele of said polymorphism with risk of statin-induced myopathy; (c) establishing a statin type and]
 (*b*) *determining a dosage for a chosen statin type* based [on said patient's statin-induced myopathy risk] *upon said presence of a C or T allele, wherein the presence of a C allele correlates with an increased risk of statin-induced myopathy*; and
 [(d)] (*c*) administering said [statin type and] dosage to said patient.

2. The method of claim 1, wherein said assaying step comprises amplifying at least part of the SLCO1B1 gene comprising said polymorphism, and identifying [the] *a* nucleotide present in at least one allele of said polymorphism in the amplified gene.

5. The method of claim 1, wherein, for a patient with [the] *a* TT genotype *for said single nucleotide polymorphism rs4149056*, said administered statin dosage is higher than the standard dosage, and for a patient with a CC or TC genotype, said statin dosage is the standard dosage.

*15. The method of claim 2, wherein amplifying involves using a polymerase chain reaction (PCR) and primers adapted to amplify said nucleotide.*

*16. The method of claim 1, wherein said assaying step comprises binding an allele specific probe to a nucleic acid sequence encoding the SLCO1B1 gene and identifying a nucleotide at said polymorphism.*

*17. The method of claim 1, wherein said assaying step comprises sequencing a nucleic acid encoding said polymorphism.*

*18. The method of claim 5, wherein for a patient with the TT genotype, 80 mg/daily of simvastatin is administered.*

*19. The method of claim 5, wherein for a patient with the TT genotype, greater than 80 mg/daily of simvastatin is administered.*

*20. The method of claim 5, wherein for a patient with the CC or TC genotype, 40 mg/daily of simvastatin or 20 mg/daily of simvastatin is administered.*

*21. The method of claim 18, wherein for a patient with the CC or TC genotype, 40 mg/daily of simvastatin or 20 mg/daily of simvastatin is administered.*

*22. The method of claim 5, wherein for a patient with the TT genotype, a two-fold or higher increase in the standard daily dosage of the statin is administered.*

*23. The method of claim 1, wherein a patient having a T allele is administered a dosage selected from 20-40 mg or greater of atorvastatin, 80-160 mg or greater of fluvastatin, 80 mg or greater of lovastatin, 80 mg or greater of pravastatin, 4 mg or greater of pitavastatin, and 20 mg or greater of rosuvastatin.*

*24. The method of claim 1, wherein a patient identified with a C allele is administered a dosage selected from 10-20 mg of atorvastatin, 40-80 mg of fluvastatin, 40 mg of lovastatin, 40 mg of pravastatin, 2 mg of pitavastatin, and 10 mg of rosuvastatin.*

*25. The method of claim 1, wherein said patient is also administered amiodarone, cyclosporine, or gemfibrozil.*

* * * * *